United States Patent
Shino

(10) Patent No.: US 12,089,803 B2
(45) Date of Patent: Sep. 17, 2024

(54) IMAGE PROCESSING DEVICE, CONTROL METHOD AND STORAGE MEDIUM

(71) Applicant: NEC Corporation, Tokyo (JP)

(72) Inventor: Ryosaku Shino, Tokyo (JP)

(73) Assignee: NEC CORPORATION, Tokyo (JP)

(*) Notice: Subject to any disclaimer, the term of this patent is extended or adjusted under 35 U.S.C. 154(b) by 193 days.

(21) Appl. No.: 17/763,778

(22) PCT Filed: Oct. 1, 2019

(86) PCT No.: PCT/JP2019/038778
§ 371 (c)(1),
(2) Date: Mar. 25, 2022

(87) PCT Pub. No.: WO2021/064867
PCT Pub. Date: Apr. 8, 2021

(65) Prior Publication Data
US 2022/0337746 A1     Oct. 20, 2022

(51) Int. Cl.
*A61B 1/00* (2006.01)
*H04N 23/50* (2023.01)
*H04N 23/698* (2023.01)

(52) U.S. Cl.
CPC .... *A61B 1/000094* (2022.02); *A61B 1/00009* (2013.01); *A61B 1/000095* (2022.02);
(Continued)

(58) Field of Classification Search
CPC .................................................. A61B 1/00094
See application file for complete search history.

(56) References Cited

U.S. PATENT DOCUMENTS

2007/0161853 A1* 7/2007 Yagi ....................... A61B 1/041
                                                                600/117
2008/0253686 A1* 10/2008 Bayer ......................... G06T 7/30
                                                                382/284
(Continued)

FOREIGN PATENT DOCUMENTS

JP     H08-249492 A      9/1996
JP     H10-113333 A      5/1998
(Continued)

OTHER PUBLICATIONS

International Search Report for PCT Application No. PCT/JP2019/038778, mailed on Dec. 10, 2019.
(Continued)

*Primary Examiner* — Irfan Habib

(57) ABSTRACT

One objective is to provide an image processing device, a control method, and a storage medium capable of suitably presenting information about a position currently being photographed in endoscopic inspection. To achieve the objective, the image processing device 1X includes a panoramic image acquiring unit 43X and a display control unit 46X. The panoramic image acquiring unit 43X acquires a panoramic image Ip, in which a wall surface in a lumen is expanded in a planar shape, based on plural captured images Ic which were acquired by photographing the lumen by a photographing unit provided in an endoscope in a first photographing process. The display control unit 46X displays on the display device 2 photographed position information relating to a photographed position of the lumen in a second photographing process in association with the panoramic image Ip.

17 Claims, 18 Drawing Sheets

(52) U.S. Cl.
CPC ......... *A61B 1/0005* (2013.01); *H04N 23/698* (2023.01); *H04N 23/555* (2023.01)

(56) References Cited

U.S. PATENT DOCUMENTS

| | | | |
|---|---|---|---|
| 2008/0262312 A1* | 10/2008 | Carroll | A61B 1/00172 600/160 |
| 2009/0074265 A1 | 3/2009 | Huang et al. | |
| 2009/0253686 A1* | 10/2009 | Glick | A61P 29/00 540/504 |
| 2011/0018871 A1 | 1/2011 | Shirahata | |
| 2011/0228994 A1 | 9/2011 | Tanaka et al. | |
| 2015/0313445 A1* | 11/2015 | Davidson | A61B 1/31 600/109 |
| 2017/0258295 A1* | 9/2017 | Kronman | A61B 1/000094 |
| 2019/0231220 A1* | 8/2019 | Refai | H04N 23/957 |
| 2020/0201022 A1* | 6/2020 | Shameli | G02B 23/243 |
| 2021/0386270 A1* | 12/2021 | Tanigami | A61B 1/07 |
| 2022/0028078 A1* | 1/2022 | Shelton | G06T 7/0012 |

FOREIGN PATENT DOCUMENTS

| | | |
|---|---|---|
| JP | 2009-226072 A | 10/2009 |
| JP | 2013-078382 A | 5/2013 |
| JP | 2015-106703 A | 6/2015 |
| JP | 2015-112431 A | 6/2015 |
| WO | 2009116465 A1 | 9/2009 |
| WO | 2010047324 A1 | 4/2010 |
| WO | 2019/087269 A1 | 5/2019 |

OTHER PUBLICATIONS

Extended European Search Report for EP Application No. 19947499, dated on Aug. 1, 2022.

JP Office Action for JP Application No. 2021-550817, mailed on Oct. 10, 2023 with English Translation.

* cited by examiner

DISTANCE Dp [mm] FROM PHOTOGRAPHING UNIT

IMAGE PROCESSING DEVICE, CONTROL METHOD AND STORAGE MEDIUM

This application is a National Stage Entry of PCT/JP2019/038778 filed on Oct. 1, 2019, the contents of all of which are incorporated herein by reference, in their entirety.

TECHNICAL FIELD

The present invention relates to a technical field of an image processing device, a control method, and a storage medium for performing processing related to display in endoscopic inspection.

BACKGROUND ART

An endoscopic system for displaying images taken in the lumen of an organ is known. For example, Patent Literature 1 discloses an endoscope system in which a synthetic expanded image of an inner wall surface of a digestive organ is generated and displayed on a display screen such as a monitor.

CITATION LIST

Patent Literature

Patent Literature 1: JP 2015-106703A

SUMMARY

Problem to be Solved by the Invention

In the case of an endoscopic inspection system in which an image indicative of a lesion part to be inspected is visually judged from a plurality of continuously acquired images, there is a possibility of missing an important part to be inspected. In order to suppress the miss or the like of such a part to be inspected, it is necessary for the inspector to accurately grasp the currently-photographed position during the inspection.

In view of the above-described issue, it is therefore an example object of the present disclosure to provide an image processing device, a control method, and a storage medium capable of appropriately presenting information on the currently-photographed position in endoscopic inspection.

Means for Solving the Problem

One mode of the image processing device is an image processing device including: a panoramic image acquiring unit configured to acquire a panoramic image, in which a wall surface in a lumen is expanded in a planar shape, based on plural captured images which were acquired by photographing the lumen by a photographing unit provided in an endoscope in a first photographing process; and a display control unit configured to display, on a display device, photographed position information in association with the panoramic image, the photographed position information relating to a photographed position of the lumen in a second photographing process.

One mode of the control method is a control method executed by an image processing device, the control method including: acquiring a panoramic image, in which a wall surface in a lumen is expanded in a planar shape, based on plural captured images which were acquired by photographing the lumen by a photographing unit provided in an endoscope in a first photographing process; and displaying, on a display device, photographed position information in association with the panoramic image, the photographed position information relating to a photographed position of the lumen in a second photographing process.

One mode of the storage medium is a storage medium storing a program executed by a computer, the program causing the computer to function as: a panoramic image acquiring unit configured to acquire a panoramic image, in which a wall surface in a lumen is expanded in a planar shape, based on plural captured images which were acquired by photographing the lumen by a photographing unit provided in an endoscope in a first photographing process; and a display control unit configured to display, on a display device, photographed position information in association with the panoramic image, the photographed position information relating to a photographed position of the lumen in a second photographing process.

Effect of the Invention

An example advantage according to the present invention is to enable an inspector to suitably grasp the photographed position in endoscopic inspection.

EXAMPLE EMBODIMENTS

Hereinafter, example embodiments of an image processing device, a control method, and a storage medium will be described with reference to the drawings.

First Example Embodiment (1) System Configuration

Figure 1:
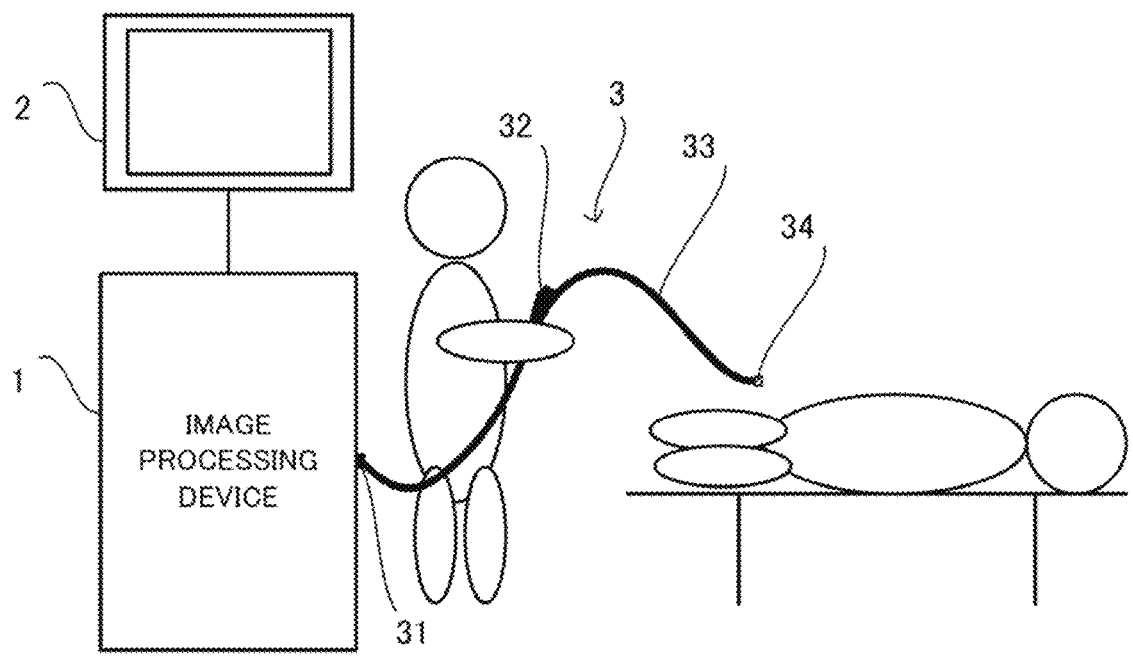
FIG. 1 illustrates the schematic configuration of an endoscopic inspection system.

FIG. 1 shows a schematic configuration of an endoscopic inspection system 100. As shown in FIG. 1, the endoscopic inspection system 100 mainly includes an image processing device 1, a display device 2, and an endoscope 3 connected to the image processing device 1. In the following, as a representative example, the process in endoscopic inspection of a large bowel will be explained.

The image processing device 1 acquires from the endoscope 3 an image (also referred to as a "captured image Ic") which the endoscope 3 captures in time series, and displays a view based on the captured image Ic on the display device 2. The captured image Ic is an image acquired by photographing the lumen of the large bowel of a subject and an image taken at predetermined time intervals in the insertion process of the endoscope 3 to the subject or the ejection process of the endoscope 3. In the present example embodiment, the image processing device 1 generates an image (also referred to as a "panoramic image Ip") in which the wall surface of the lumen is expanded (unfolded) into a plane based on a plurality of captured images Ic which indicate substantially the entire lumen of the large bowel in pieces and which are generated in the insertion process or the ejection process of the endoscope 3 in the past endoscopic inspection. Then, in the second endoscopic inspection for the subject, the image processing device 1 displays, on the display device 2, the information on the photographed position, that is the currently-photographed position by the endoscope 3, in association with the panoramic image Ip. Details of this process will be described later. Hereinafter, a process (that is, the insertion process or the ejection process of the endoscope 3) of generating a series of captured images Ic which indicate substantially the entire lumen to be photographed in pieces (in piecemeal manner) is also referred to as "photographing process".

The display device 2 is a display or the like for displaying information based on a display signal supplied from the image processing device 1.

The endoscope 3 is the device which photographs the lumen of the large bowel in a state of being inserted in the subject's large bowel. The endoscope 3 mainly includes a connecting unit 31 for connecting with the image processing device 1, an operation unit 32 for inspector to perform a predetermined input, a shaft 33 having flexibility and to be inserted into the lumen, and a pointed end unit 34 having a built-in photographing unit such as an ultra-small image pickup device. The operation unit 32 includes, for example, adjustable dial unit configured to perform stepwise adjustment of a direction in two axes (referred to as "X-axis" and "Y-axis") perpendicular to each other on the vertical plane of the pointed end unit 34. Further, the operation unit 32 includes, for example, a button or the like for specifying an attention part, such as a part (simply referred to as "lesion part") to be suspected as lesion formation, when the inspector finds out the attention part. In this case, for example, the inspector refers to the captured image Ic displayed by the display device 2 during the inspection and then, if an attention part is displayed on the captured image Ic, the inspector selects the above-described button to thereby specify that the currently-displayed captured image Ic includes an attention part. If the button described above is selected, the operation unit 32 supplies a predetermined signal (also referred to as "operation signal S1") to the image processing device 1.

(2) Hardware Configuration

Figure 2:
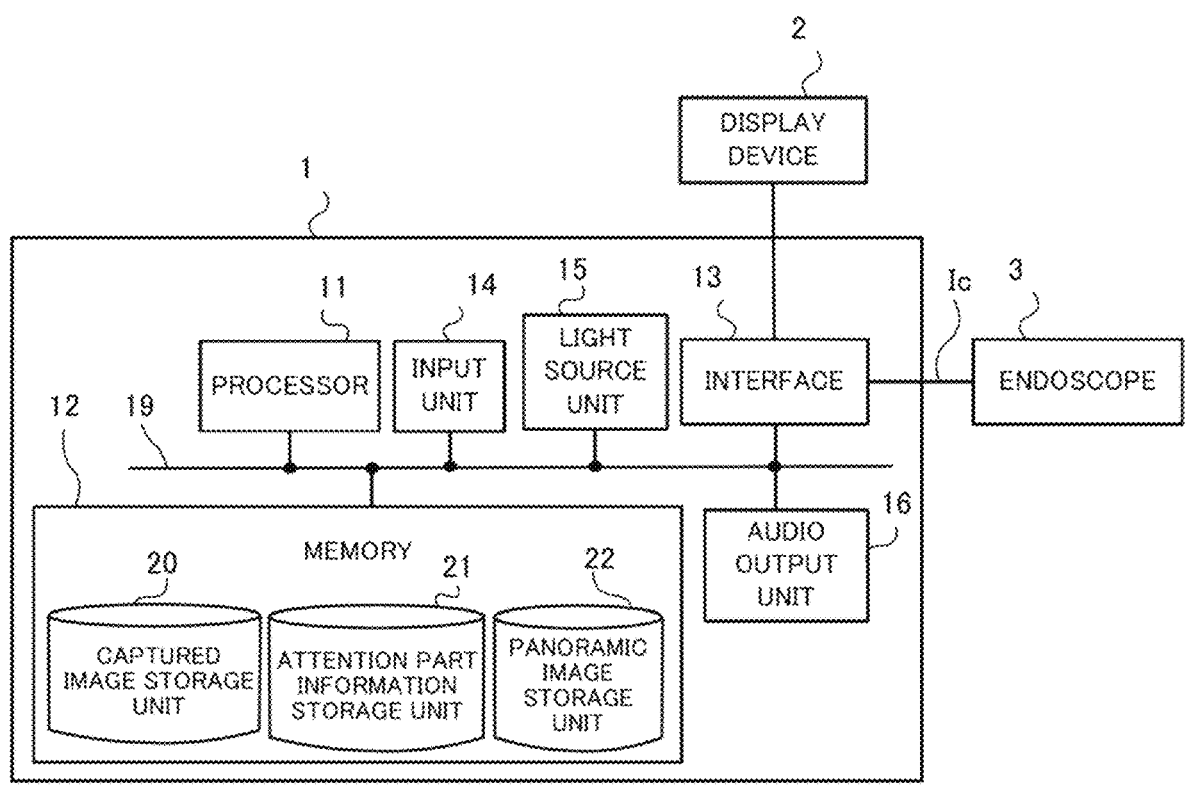
FIG. 2 illustrates the hardware configuration of an image processing device.

FIG. 2 shows the hardware configuration of the image processing device 1. The image processing device 1 mainly includes a processor 11, a memory 12, an interface 13, an input unit 14, a light source unit 15, and an audio output unit 16. Each of these elements is connected to one another via a data bus 19.

The processor 11 executes a predetermined process by executing a program or the like stored in the memory 12. The processor 11 is one or more processors such as a CPU (Central Processing Unit) or a GPU (Graphics Processing Unit).

The memory 12 is configured by various memories (storage media) such as a RAM (Random Access Memory), a ROM (Read Only Memory). The memory 12 may be an external storage device such as a hard disk connected to or built in to the image processing device 1, or may be a storage medium such as a flash memory. The memory 12 stores a program for the image processing device 1 to execute each processing in the present example embodiment. The memory 12 functionally includes a captured image storage unit 20, an attention part information storage unit 21, and a panoramic image storage unit 22. Details of these storage units will be described later. The memory 12 is also used as a work memory.

The interface 13 includes an interface for connecting the image processing device 1 and the display device 2, and an interface for connecting the image processing device 1 and the endoscope 3. For example, interface 13 provides a display signal generated by processor 11 to display device 2. Further, the interface 13 supplies the light generated by the light source unit 15 and the like to the endoscope 3. The interface 13 also provides the processor 11 with an electrical signal indicative of the captured image Ic supplied from the endoscope 3. When the captured image storage unit 20, the attention point information storage unit 21, and the panoramic image storage unit 22 are included in an external storage device, the interface 13 includes an interface that conforms to, for example, USB or SATA (Serial AT Attachment).

The input unit 14 generates an input signal based on the operation by the inspector. Examples of the input unit 14 include a button, a touch panel, a remote controller, a voice input device. The light source unit 15 generates light to be supplied to the pointed end unit 34 of the endoscope 3. The light source unit 15 may also incorporate a pump or the like for delivering water and air to be supplied to the endoscope 3. The audio output unit 16 outputs a sound under the control of the processor 11.

(3) Data Overview

Next, an outline of the data stored in the captured image storage unit 20, the attention part information storage unit 21, and the panoramic image storage unit 22 will be described.

The captured image storage unit 20, under the control of the processor 11, stores a series of captured images Ic acquired by photographing the entire lumen of the large bowel in the photographing process (insertion process or ejection process) in endoscopic inspection. These captured images Ic are images to be used for generating the panoramic image Ip and are stored in association with the subject's identification information (e.g., patient ID). In addition, time stamp information for identifying the photographing process and the photographing order among the images is associated with each captured image Ic.

In general, the endoscope 3 can move more smoothly in the lumen during the ejection process than during insertion process of the endoscope 3. Accordingly, the captured image Ic generated in the ejection process of the endoscope 3 indicates more clearly on the inside of the lumen than the captured image Ic generated in the insertion process of the endoscope 3. Thus, in some embodiments, the processor 11 stores in the captured image storage unit 20 a series of captured images Ic acquired by photographing the lumen of the large bowel in the ejection process of the endoscope 3 so as to use for generating a panoramic image Ip.

The attention part information storage unit 21 stores information (also referred to as "attention part information") indicating an attention part that is a point to be paid attention to during the inspection in the lumen of the large bowel subjected to inspection. Examples of the attention parts include a part designated by an inspector as a lesion (defective or diseased) part and a part detected by an image analysis program for detecting a lesion part. It is noted that examples of the attention part not only include a lesion part but also include an inflammation part, a point with an operating mark or other cuts, a point with a fold or a protrusion, a contact point where the pointed end unit 34 got contact (caught) with the wall surface of the lumen in the previous inspection. Examples of the attention part information include a captured image Ic itself indicative of the attention part, a partial image acquired by cropping the attention part from the captured image Ic, and information regarding a feature point in the lumen which overlaps or is closest to the attention part. A method of extracting a feature point and the like will be described later. In addition, the attention part information may further include type information regarding the attention part, such as information indicating whether the attention part is an abnormal part such as a lesion part or a contact point of the endoscope 3 during the previous insertion process.

The panoramic image storage unit 22 stores a panoramic image Ip generated by the processor 11. After the captured images Ic necessary for generating the panoramic image Ip is stored in the captured image storage unit 20, the processor 11 generates the panoramic image Ip at a predetermined timing, and stores the generated panoramic image Ip in the panoramic image storage unit 22 in association with the identification information or the like of the subject. In addition, in some embodiments, the panoramic image Ip may be associated with information relating to the shooting date and time (time stamp) of the captured images Ic used for generating the panoramic image Ip, and identification information of the subject. In addition to the panoramic image Ip, the panoramic image storage unit 22 may further store information regarding feature points extracted from each captured image Ic at the time of generating the panoramic image Ip. Information on this feature point is used, for example, in the calculation of the distance between two points in the lumen.

(4) Functional Block

Figure 3:
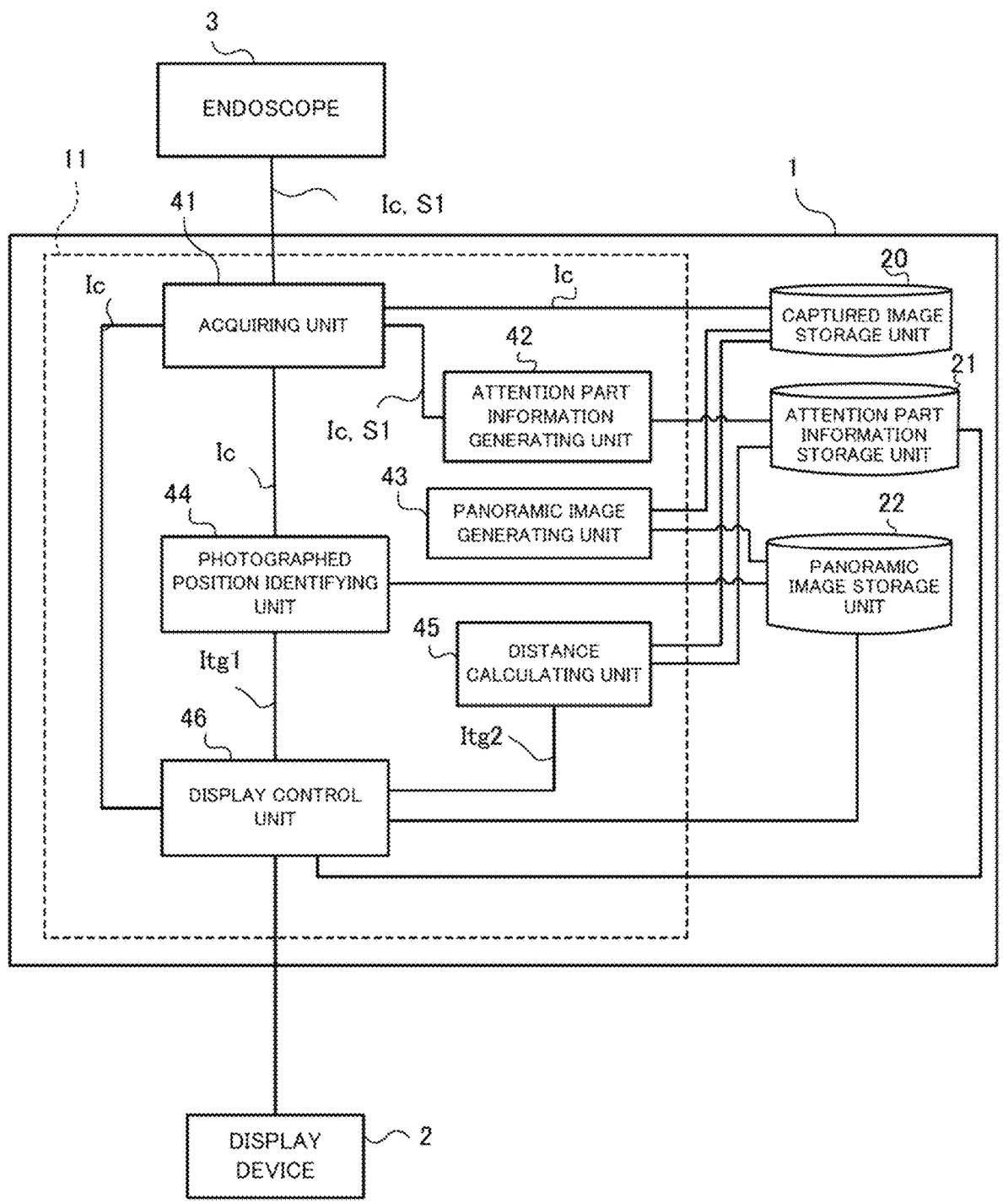
FIG. 3 illustrates a functional block diagram of an image processing device.

FIG. 3 is a functional block diagram of the image processing device 1. As shown in FIG. 3, the processor 11 of the image processing device 1 functionally includes an acquiring unit 41, an attention part information generating unit 42, a panoramic image generating unit 43, a photographed position identifying unit 44, a distance calculating unit 45, and a display control unit 46.

The acquiring unit 41 acquires a captured image Ic taken by the endoscope 3 via the interface 13 at predetermined intervals. Then, the acquiring unit 41 stores the acquired captured image Ic in the captured image storage unit 20 in association with the subject's identification information and the like. In this case, for example, the acquiring unit 41 acquires the subject's identification information on the basis of the input information generated by the input unit 14 by the time the inspection starts, and then adds the information to the captured image Ic acquired from the endoscope 3. Further, the acquiring unit 41 supplies the acquired captured image Ic to the display control unit 46. The captured image Ic is immediately displayed on the display device 2.

Furthermore, if the captured images Ic taken in the past endoscopic inspection for the same subject are stored in the captured image storage unit 20, the acquiring unit 41 supplies the acquired captured image Ic to the photographed position identifying unit 44. Further, when receiving the operation signal S1 specifying an attention part from the endoscope 3, the acquiring unit 41 supplies the attention part information generation unit 42 with the operation signal S1 and the captured image Ic, which is received from the endoscope 3 at the same receipt timing as the operation signal S1.

The attention part information generating unit 42 generates the attention part information based on the captured image Ic and the operation signal S1 which are supplied from the acquiring unit 41, and stores the generated attention part information in the attention part information storage unit 21. For example, the attention part information generating unit 42 determines that the captured image Ic supplied from the endoscope 3 together with the operation signal S1 represents an attention part such as a lesion part, and stores the captured image Ic as the attention part information in the attention part information storage unit 21. In another example, the attention part information generating unit 42 executes an image analysis program for detecting a lesion part and the like with respect to the captured image Ic supplied from the acquiring unit 41. Then, when the attention part information generating unit 42 detects an attention part such as a lesion part in the captured image Ic, it stores the attention part information indicating the detected attention part in the attention part information storage unit 21. The attention part information in this case may be the captured image Ic itself in which the attention part is detected, or may be feature quantity information representing the attention part. Here, the image analysis program for detecting a lesion part and the like, for example, may be a program based on any algorithm to be used for abnormality detection (so-called anomaly detection).

In yet another example, the attention part information generating unit 42 detects, as an attention part, a point (also referred to as a "contact point") where the pointed end unit 34 of the endoscope 3 got caught (contact with the wall surface) in the insertion process of the endoscope 3. Then, the attention part information generating unit 42 stores the attention part information indicating the detected attention part in the attention part information storage unit 21. In this case, the intended point information generating unit 42 may detect the contact point through image analysis with respect to the captured image Ic, or if the contact sensor or the like is provided at the pointed end unit 34, it may detect the contact point by the sensor. For example, in the case of the former, the attention information generating unit 42 uses, as the attention information, the captured image Ic taken when the jamming of the pointed end unit 34 occurs, and in the case of the latter, it uses, as the attention point information, the captured image Ic generated when the sensor detects the contact.

In some embodiment, the attention part information generating unit 42 may include the type information of the detected attention part in the attention part information. For example, when the attention part information generating unit 42 has detected the contact point based on the image analysis described above or the output of the contact sensor, the attention part information generating unit 42 includes, in the attention part information, identification information indicating that the contact point is the attention part. Similarly, when in the attention part information has detected a lesion part (or other abnormal part) on the basis of the operation signal S1 or the image analysis program for detecting the abnormality, the attention part information generating unit 42 includes, in the attention part information, identification information representing a lesion part.

The panoramic image generating unit 43 generates a panoramic image Ip in which the entire lumen of the large bowel of the subject is unfolded (expanded) into a planar shape on the basis of the captured images Ic stored in the captured image storage unit 20. Details of the generating process of the panoramic image Ip by the panoramic image generating unit 43 will be described later. The panoramic image generating unit 43 stores the generated panoramic image Ip in the panoramic image storage unit 22. At this time, for example, the panoramic image generating unit 43 stores the shooting date and the generation time of the captured images Ic used for generating the panoramic image Ip, and information for identifying the subject in association with the panoramic image Ip.

Here, a supplementary description will be given of the generation timing of the panoramic image Ip. For example, the panoramic image generating unit 43 generates a panoramic image Ip based on these captured images Ic just after a series of captured images Ic captured in the photographing process of the endoscopic inspection are stored in the captured image storage unit 20. In another example, the panoramic image generating unit 43 acquires the captured images Ic of the subject from the captured image storage unit 20 and generates the panoramic image Ip when there is a generation instruction of the panoramic image Ip from the display control unit 46. In the latter example, the panoramic image generating unit 43 may directly supply the generated panoramic image Ip to the display control unit 46 after generating the panoramic image Ip based on the generation instruction of the panoramic image Ip from the display control unit 46.

The photographed position identifying unit 44 specifies the current photographed position in the panoramic image Ip based on the latest captured image Ic for the subject and the panoramic image Ip representing the lumen of the subject. The photographed position identifying unit 44, for example, in this case, performs verification (matching) between the captured image Ic supplied from the acquiring unit 41 and the above-described panoramic image Ip to thereby specify an area corresponding to the captured image Ic in the panoramic image Ip. Then, the photographed position identifying unit 44 supplies information indicating the specified area in the panoramic image Ip corresponding to the captured image Ic to the display control unit 46 as the first photographed position information "Itg1".

A supplemental description will be given of the verification of the captured image Ic with the panoramic image Ip. For example, the photographed position identifying unit 44 converts the captured image Ic into an image in which the wall surface of the lumen is unfolded (expanded) as with the panoramic image Ip, and then performs the above-described verification with the converted image and the panoramic image Ip. In this case, the photographed position identifying unit 44 extracts the feature points of the panoramic image Ip and the captured image Ic, respectively, and performs matching of the feature points, thereby specifying the area in the panoramic image Ip corresponding to the captured image Ic. Specific processing of extraction of feature points and matching of feature points will be described in the explanation of a panoramic image generating process and a distance calculation process to be described later.

The distance calculating unit 45 calculates a distance between any two points in the lumen of the subject based on the captured image Ic. The distance between the two points calculated by the imaging position identifying unit 44 shall refer to the distance along the lumen. In the present example embodiment, the distance calculating unit 45 calculates, as the distance between the two points in the lumen, the distance between any two points selected from: the insertion position of the endoscope 3 (i.e., the position of the anal); the photographed position by the endoscope 3; and attention parts such as a lesion part and a contact point. The calculation method of the distance between the two points by the distance calculating unit 45 will be described later. The distance calculating unit 45 supplies the display control unit 46 with the information indicating the calculated distance as second photographed position information "Itg2".

The display control unit 46 generates a display signal relating to the endoscopic inspection and supplies the generated display signal to the display device 2 to thereby display a view relating to the endoscopic inspection on the display device 2. Specifically, the display control unit 46 acquires the panoramic image Ip corresponding to the subject from the panoramic image storage unit 22 and displays the acquired panoramic image Ip on the display device 2. In this case, on the basis of the first photographed position information Itg1 received from the photographed position identifying unit 44, the display control unit 46 displays the photographed position in association with the panoramic image Ip. Further, on the basis of the second photographed position information Itg2 received from the distance calculating unit 45, the display control unit 46 displays the distance from the insertion position of the endoscope 3 to the photographed position in association with the panoramic image Ip. Further, with reference to the attention part information storage unit 21, the display control unit 46 highlights one or more attention parts to be noticed (or paid attention to) by the inspector on the panoramic image Ip. In addition, the display control unit 46 displays various information for assisting the inspector's work. Specific display examples of the display device 2 will be described later. If the endoscopic inspection for the subject has not been performed in the past and therefore it is impossible to acquire the panoramic image Ip to be displayed, the display control unit 46 displays the captured image Ic supplied from the acquiring unit 41 on the display device 2. Further, when the endoscopic inspection for the subject has been performed a plurality of times in the past, the display control unit 46 may display on the display device the panoramic image Ip based on the captured images Ic generated in the immediately preceding endoscopic inspection for the subject.

(5) Display Example

Next, details of the processing performed by the display control unit 46 will be described with reference to FIGS. 4 to 7.

Figure 4:
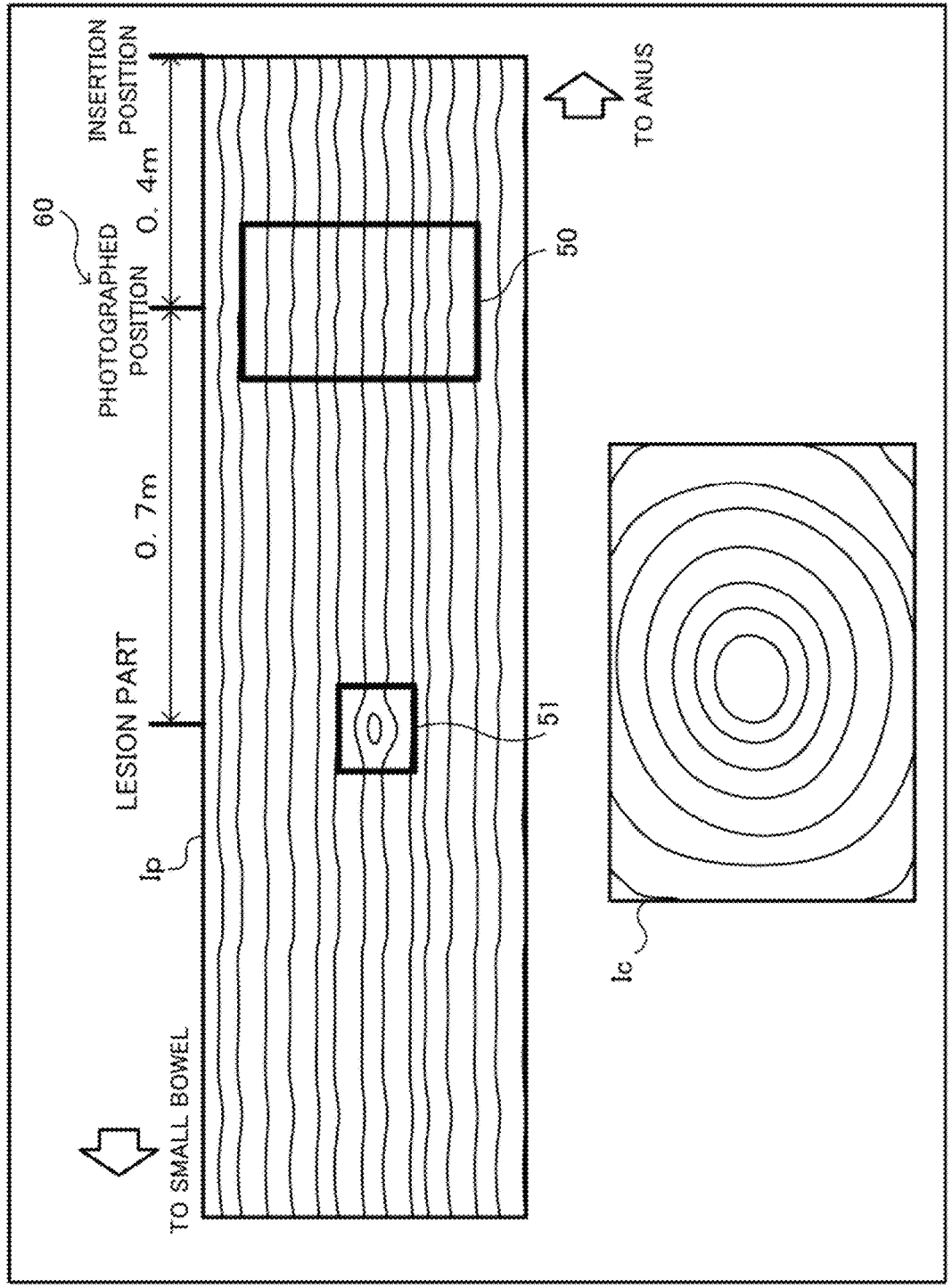
FIG. 4 illustrates a first display example displayed by a display device in endoscopic inspection.

FIG. 4 is a first display example of a view displayed by the display device 2 based on the display signal generated by the display control unit 46 in the endoscopic inspection. The first display example shows a display view on the display device 2 when the endoscopic inspection for a subject who has undergone the endoscopic inspection in the past is being performed again.

In the first display example, the display control unit 46 displays on the display device 2 the panoramic image Ip generated based on the captured images Ic acquired in the previous endoscopic inspection for the same subject. Here, the panoramic image Ip becomes the global image in which the inner wall of the subject's large bowel is expanded (unfolded). Further, the display control unit 46 acquires the captured image Ic generated by the endoscope 3 in real time in the current endoscopic inspection and displays it together with the panoramic image Ip on the display device 2.

In the first display example, the display control unit 46 displays, in association with the panoramic image Ip, a photographed position mark 50 indicating the current photographed position, a lesion part mark 51 indicating an attention point (here, a lesion part) detected in the first endoscopic inspection, and a distance information 60 indicating the distance between two points along the lumen.

In this case, on the basis of the first photographed position information Itg1 generated by the photographed position identifying unit 44, the display control unit 46 displays, on the panoramic image Ip, the photographed position mark 50 which surrounds the photographed position identified by the photographed position identifying unit 44. Here, as an example, the display control unit 46 displays, on the panoramic image Ip, the smallest rectangle including the corresponding part of the latest captured image Ic acquired from the endoscope 3 in the panoramic image Ip as the photographed position mark 50. Further, the distance calculating unit 45 acquires from the captured image storage unit 20 a series of captured images Ic to be used for generating the panoramic image Ip subjected to display, and calculates the distance (here, 0.4m) from the insertion position (i.e., the anal) of the endoscope 3 to the photographed position. Then, on the basis of the second photographed position information Itg2 generated by the distance calculating unit 45, the display control unit 46 displays the distance information 60 indicating the distance from the insertion position of the endoscope 3 to the photographed position in association with the panoramic image Ip.

In this way, the display control unit 46 displays the photographed position mark 50 in association with the panoramic image Ip. Thereby, it is possible to let the inspector recognize the current photographed position in the entire large bowel. Further, the display control unit 46 displays the distance (here, 0.4m) from the insertion position (i.e., the anal) of the endoscope 3 to the photographed position, thereby allowing the inspector to grasp the current photographed position more accurately.

Further, the display control unit 46 refers to the attention part information indicating the attention part (here, the lesion part) generated at the time of the previous endoscopic inspection for the subject stored in the attention part information storage unit 21, and displays the lesion part mark 51 surrounding the lesion part on the panoramic image Ip. Here, as an example, the display control unit 46 identifies the target lesion part by matching the captured image Ic or the like stored as the attention part information with the panoramic image Ip, and displays the smallest rectangle surrounding the identified lesion part on the panoramic image Ip as the lesion part mark 51. Further, the distance calculating unit 45 acquires the captured images Ic used for generating the panoramic image Ip from the captured image storage unit 20, and calculates the distance (here, 0.7m) from the photographed position to the lesion part that is an attention point. Then, on the basis of the second photographed position information Itg2 generated by the distance calculating unit 45, the display control unit 46 displays, in association with the panoramic image Ip, the distance information 60 representing the distance from the photographed position to the lesion part that is an attention point.

In this way, the display control unit 46 displays the lesion part mark 51 together with the photographed position mark 50 in association with the panoramic image Ip. Thereby, it is possible to appropriately allow the inspector to recognize the relative positional relationship between the current photographed position and the attention part (the lesion part) in the entire large bowel. Further, the display control unit 46 displays the distance (here 0.7m) from the photographed position to the lesion part that is an attention point. Thereby, it is possible to suitably provide the inspector with a reference for guiding the photographed position to the lesion part. It is noted that the display shown in FIG. 4 has a function equivalent to the display to be used for route guidance for the vehicle or the like, and suitably contributes to navigation with respect to the endoscope 3. In this case, the panoramic image Ip corresponds to a map representing the entire large bowel to be inspected, the photographed position mark 50 corresponds to the current position mark, and the lesion part mark 51 corresponds to the mark of the destination.

Figure 5:
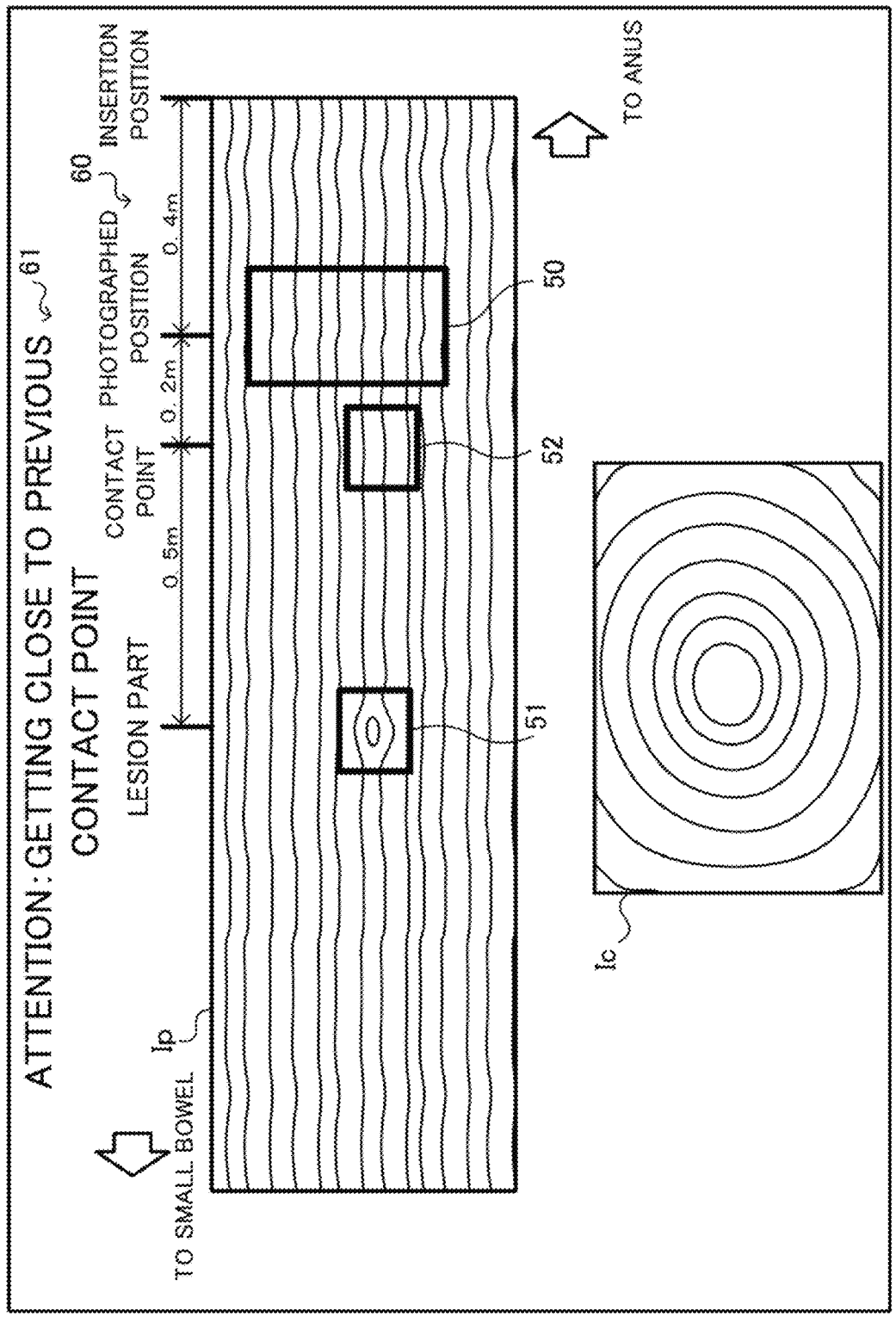
FIG. 5 illustrates a second display example displayed by a display device in endoscopic inspection.

FIG. 5 is a second display example of a view displayed by display device 2 based on the display signal generated by the display control unit 46. The second display example shows a display view on the display device 2 when the endoscopic inspection for a subject who has undergone the endoscopic inspection in the past is being performed again.

In the second display example, the display control unit 46 displays the photographed position mark 50 and the lesion part mark 51 in association with the panoramic image Ip in the same manner as in the first display example. In addition, the display control unit 46 displays the contact point mark 52 indicating the contact point detected at the time of the previous inspection for the same subject in association with the panoramic image Ip.

In this case, the display control unit 46 extracts the attention part information generated during the previous inspection for the subject from the attention part information storage unit 21. In this case, the extracted attention point information indicates a lesion part and a contact point, respectively, and the display control unit 46 identifies the lesion part and the contact point on the panoramic image Ip, respectively, by matching these attention point information with the panoramic image Ip. Then, the display control unit 46 displays the contact point mark 52 surrounding the identified contact point together with the lesion part mark 51 surrounding the identified lesion part in association with the panoramic image Ip. Further, by using the captured images Ic generated at the time of the previous inspection for the same subject stored in the captured image storage unit 20, the distance calculating unit 45 calculates the distance from the insertion position of the endoscope 3 to the photographed position (0.4m), the distance from the photographed position to the contact point (0.2m), and the distance from the contact point to the lesion part (0.5m), respectively. The display control unit 46 displays the distance information 60 indicating these distances calculated by the distance calculating unit 45 in association with the panoramic image Ip.

In this way, the display control unit 46 identifies the contact point where the insertion of the endoscope 3 was not smoothly performed in the insertion process of the previous inspection, and clearly indicates the contact point on the panoramic image Ip by the contact point mark 52. Thereby, it is possible to allow the inspector to suitably recognize the position where attention is required in the insertion of the endoscope 3. Further, the display control unit 46 displays the distance between the contact point and the photographed position in association with the panoramic image Ip. Thereby, it is possible to allow the inspector to more accurately recognize the positional relationship between the contact point and the photographed position.

In the second display example, the display control unit 46 detects that the distance between the contact point and the photographed position is equal to or less than a predetermined threshold value (e.g., 0.2m) determined in advance, and therefore displays, on the display device 2, text information 61 indicating an attention (caution) that the photographed position is getting close to the contact point. Thereby, the display control unit 46 informs the inspector that the pointed end unit 34 is approaching the contact point, and therefore can suitably call for the attention regarding the insertion operation of the endoscope 3. Further, in addition to the display of the text information 61, the display control unit 46 may output the same contents as the text information 61 by the audio output unit 16.

In some embodiments, if the distance between the lesion part and the photographed position is equal to or less than a predetermined threshold value, the display control unit 46 may also display on the display device 2 the text information indicating an attention that the photographed position is approaching the lesion part. The threshold value described above is determined in advance through experimental trials, for example, so that the attention becomes an optimum timing for the inspector. Thereby, the display control unit 46 can reliably suppress the inspector from missing a lesion part. In addition to the above-described display, the display control unit 46 may output an attention indicating that the photographed position is approaching the lesion part by the audio output unit 16.

Figure 6:
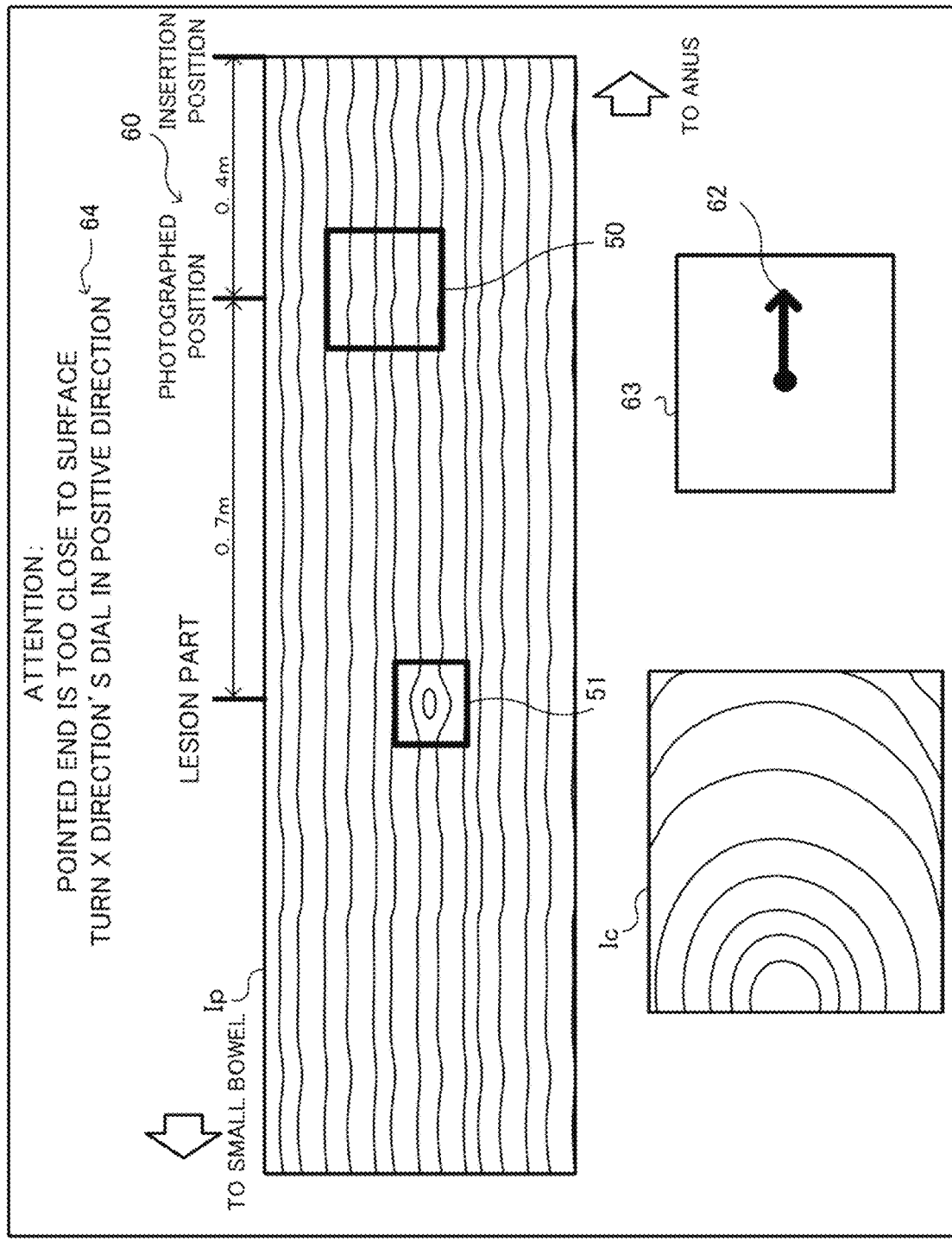
FIG. 6 illustrates a third display example displayed by a display device in endoscopic inspection.

FIG. 6 is a third display example displayed on the display device 2 based on the display signal generated by the display control unit 46. The third display example shows a display view on the display device 2 in the insertion process of the endoscope 3 when the endoscopic inspection for a subject who has undergone the endoscopic inspection in the past is being performed again.

The display control unit 46, as in the first display example and the second display example, displays the photographed position mark 50 and the lesion part mark 51 in association with the panoramic image Ip. In addition, the display control unit 46 displays the photographing direction arrow 62 indicating the direction (line-of-sight direction) of the photographing unit, which is built in the pointed end unit 34, in the rectangle 63. Here, the photographing direction arrow 62 indicates a difference in the photographing direction of the photographing unit with respect to the central direction of the lumen (i.e., the direction of stretching of the lumen). Specifically, the direction of the photographing direction arrow 62 indicates the direction of the deviation of the photographing direction of the photographing unit with respect to the central direction of the lumen, and the length of the photographing direction arrow 62 indicates the magnitude of the deviation. For example, the horizontal and vertical directions of the rectangle 63 surrounding the photographing direction arrow 62 may correspond to the X-axis and the Y-axis indicating the two axes for adjusting the orientation of the pointed end unit 34 by using the dial part of the operation unit 32, respectively, or may correspond to the horizontal and vertical directions in the captured image Ic, respectively. The horizontal and vertical directions in the captured image Ic may be in the same direction as the above-described X-axis and Y-axis for adjusting the orientation of the pointed end unit 34, respectively.

Then, the display control unit 46 calculates the deviation of the photographing direction of the photographing unit with respect to the central direction of the lumen, for example, through an image analysis on the latest captured image Ic acquired from the endoscope 3. In this case, the display control unit 46, for example, detects the farthest point in the lumen, and estimates the deviation of the photographing direction of the photographing unit with respect to the central direction of the lumen based on the position of the farthest point. Then, on the basis of the calculated deviation, the display control unit 46 determines the direction and size of the photographing direction arrow 62. When the horizontal and vertical directions of the rectangle 63 do not correspond to the horizontal and vertical directions of the captured image Ic, the display control unit 46 converts the deviation of the photographing direction of the photographing unit calculated from the captured image Ic to a deviation with respect to the horizontal and vertical directions of the rectangle 63 to thereafter determine the direction and size of the photographing direction arrow 62. In this case, the display control unit 46, for example, stores in advance information for converting the deviation with respect to the horizontal and vertical directions of the captured image Ic to the deviation with respect to the horizontal and vertical directions of the rectangle 63.

Furthermore, in the third display example, the display control unit 46 detects that the wall surface of the lumen and the pointed end unit 34 are getting close within a predetermined distance, and therefore displays, on the display device 2, text information 64 indicating an attention that the pointed end unit 34 is too close to the wall surface. At this time, the display control unit 46 displays on the display device 2 the text information 64 not only including the attention indicating that the pointed end unit 34 is too close to the wall surface but also including instruction information ("TURN X DIRECTION'S DIAL IN POSITIVE DIRECTION") for instructing a specific operation at the operation unit 32.

In this case, the display control unit 46 performs any of known image analysis approaches on the latest captured image Ic acquired from the endoscope 3 to thereby calculate the distance between the pointed end unit 34 and the wall surface displayed on the captured image Ic. Then, if the calculated distance is equal to or smaller than a predetermined threshold value, the display control unit 45 outputs the above-described attention. The threshold value described above is predetermined based on, for example, experiments or the like. When a sensor (such as proximity sensor) other than the photographing unit is provided at the pointed end unit 34, the display control unit 46 may calculate the distance described above based on the output of the sensor. In this case, for example, the display control unit 46 displays, as a part of the text information 64, instruction information indicating that the direction of the pointed end unit 34 should be adjusted in a direction opposite to the direction indicated by the photographing direction arrow 62. In addition to the display of the text information 64, the display control unit 46 may output the contents equivalent to the text information 64 by the audio output unit 16.

In this way, in the third display example, the display control unit 46 indicates the deviation of the current photographing direction by the photographing direction arrow 62. Thereby, it is possible to suitably support the insertion operation of the endoscope 3 by the inspector. Further, when detecting that the pointed end unit 34 is approaching the wall surface, the display control unit 46 outputs an attention and instruction information relating to the operation for the endoscope 3. Thereby, it is possible to allow the inspector to smoothly execute the insertion operation of the endoscope 3.

Figure 7:
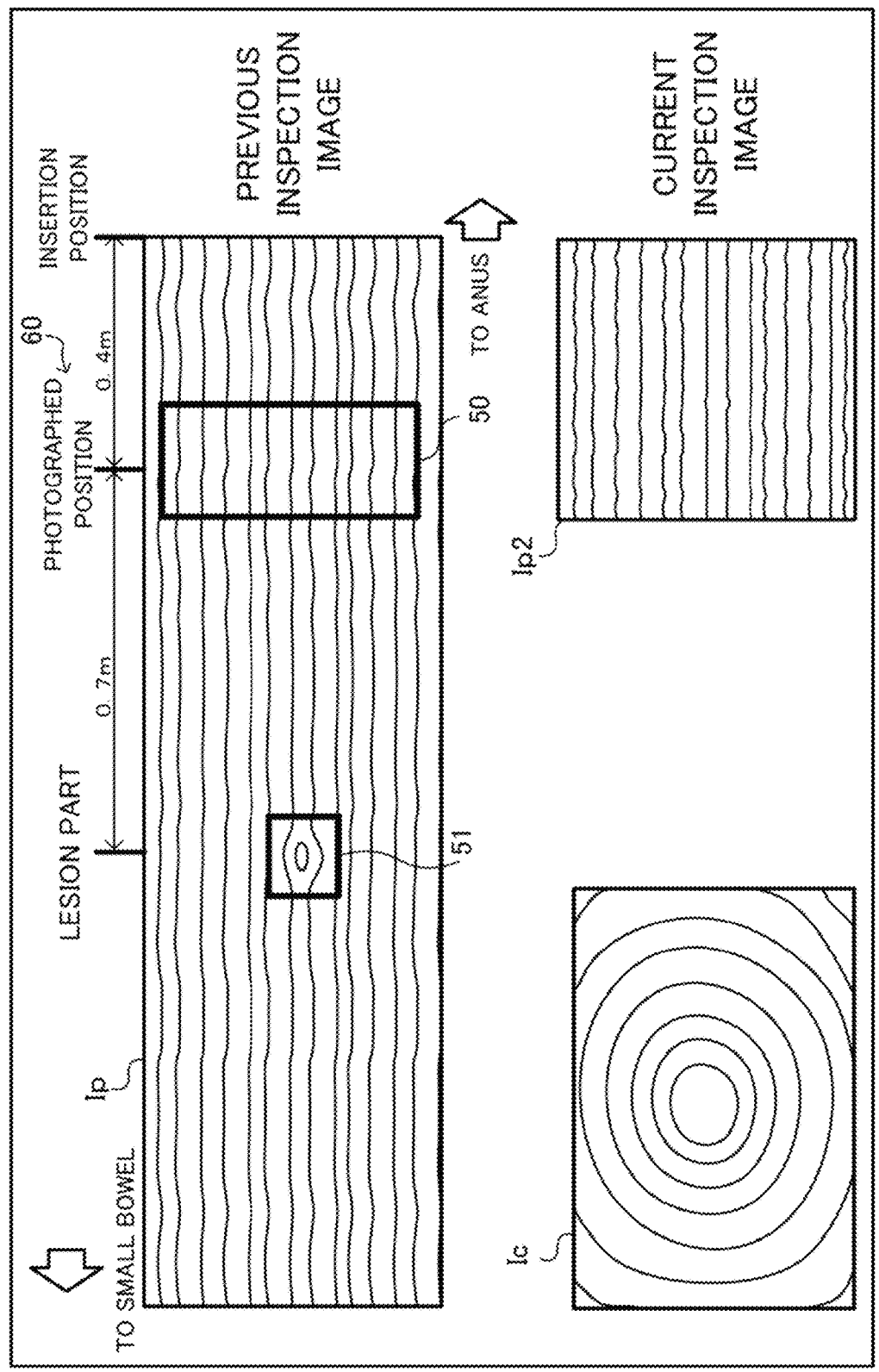
FIG. 7 illustrates a fourth display example displayed by a display device in endoscopic inspection.

FIG. 7 is a fourth display example displayed on the display device 2 based on the display signal generated by the display control unit 46. The fourth display example shows a display view on the display device 2 when the endoscopic inspection for a subject who has undergone the endoscopic inspection in the past is being performed again.

In the fourth display example, the display control unit 46 not only displays the panoramic image Ip based on the captured images Ic generated in the previous endoscopic inspection but also displays on the display device 2 a panoramic image (also referred to as "second panoramic image Ip2") based on the captured images Ic generated during the ongoing endoscopic inspection. In this case, the panoramic image generating unit 43 extracts the captured images Ic generated in the present inspection from the captured image storage unit 20 or directly acquires the captured images Ic from the acquiring unit 41, and performs a panoramic image generating process to be described later with respect to the captured images Ic to generate the second panoramic image Ip2. In this case, for example, the panoramic image generating unit 43 performs a panoramic image generating process at predetermined time intervals and updates the second panoramic image Ip2 to be displayed on the display device 2. According to the fourth display example, the display control unit 46 can present to the inspector the past state of the lumen of the subject in the past endoscopic inspection and the current state of the lumen of the subject in the ongoing endoscopic inspection so as for the inspector to suitably compare them.

(6) Overall Processing Overview

Figure 8:
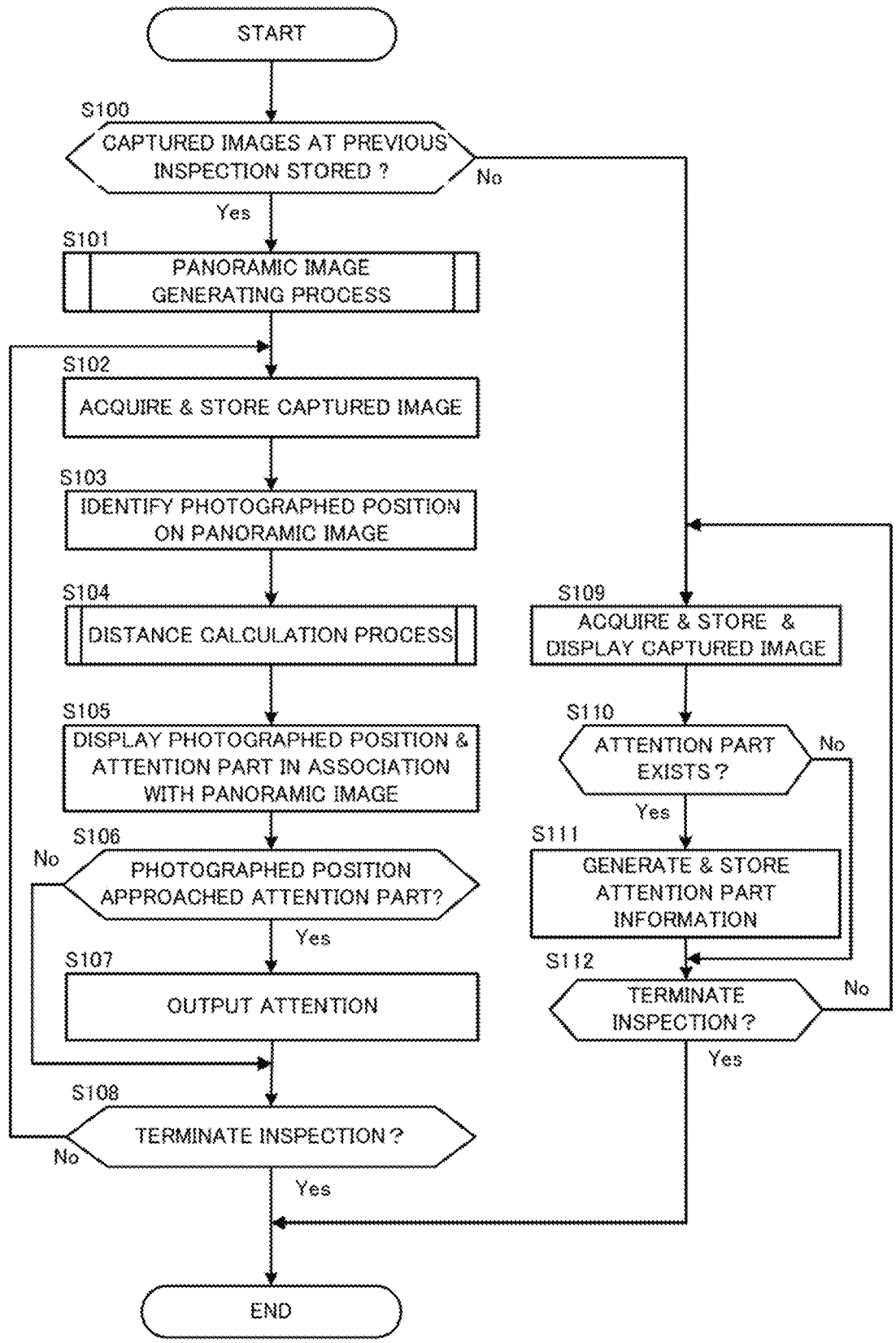
FIG. 8 illustrates an example of a flowchart showing an outline of the display processing in endoscopic inspection.

FIG. 8 is an example of a flowchart showing an outline of a display process according to the present example embodiment performed by the image processing device 1 at the time of endoscopic inspection. The image processing device 1 performs processing in FIG. 8, for example, when the insertion process or ejection process of the endoscope 3 in endoscopic inspection has started. In this case, the image processing device 1 determines that the processing in FIG. 8 should be started, for example, when there is a predetermined input through the input unit 14 or the operation unit 32.

First, the image processing device 1 determines whether or not the captured images Ic acquired during the previous inspection for the target subject of the ongoing endoscopic inspection are stored in the captured image storage unit 20 (step S100). If the captured images Ic generated during the previous inspection for the same subject are stored in the captured image storage unit 20 (step S100; Yes), the panoramic image generating unit 43 executes the panoramic image generating process (step S101). Thereby, the panoramic image generating unit 43 generates a panoramic image Ip in which the lumen of the large bowel of the subject is globally expanded based on a series of captured images Ic acquired in the photographing process at the time of the previous inspection. The panoramic image generating unit 43 may perform the panoramic image generating process at step S101 at any timing from the time of the previous inspection to the time of the present inspection, and store the generated panoramic image Ip in the panoramic image storage unit 22.

Next, the acquiring unit 41 acquires the captured image Ic acquired in real time from the endoscope 3, and stores the acquired captured image Ic in the captured image storage unit 20 (step S102). Then, the photographed position identifying unit 44 identifies the present photographed position on the panoramic image Ip by performing verification between the latest captured image Ic acquired from the endoscope 3 and the panoramic image Ip generated at step S101 (step S103). Further, the distance calculating unit 45 executes the distance calculation process of calculating the distance along the lumen between the two points in the lumen (step S104). Thereby, the distance calculating unit 45 calculates the distance from the insertion position of the endoscope 3 to the photographed position, the distance from the photographed position to the attention point, and the like.

Then, the display control unit 46 displays the current photographed position and the attention point on the display device 2 in association with the panoramic image Ip based on the processing result at step S103 and step S104 and the panoramic image Ip generated at step S101 (step S105). Thereby, the display control unit 46 can suitably allow the inspector to recognize the positional relationship between the current photographed position and the attention point on the entire lumen.

Then, the display control unit 46 determines whether or not the photographed position has approached the attention point within a predetermined distance (step S106). If it is determined that the photographed position has approached the attention point within the predetermined distance (step S106; Yes), the display control unit 46 outputs an attention indicating that the photographed position is getting close to the attention point (step S107). In this case, the display control unit 46 may display the above attention on the display device 2, or may output the attention by the audio output unit 16.

Then, when the step S107 is terminated, or when the photographed position has not approached the attention point within the predetermined distance (step S106; No), the image processing device 1 determines whether or not the ongoing endoscopic inspection has been terminated (step S108). For example, the image processing device 1 determines that the ongoing endoscopic inspection has been terminated when a predetermined input or the like through the input unit 14 or the operation unit 32 is detected. When determining that the ongoing endoscopic inspection has been terminated (Step S108; Yes), the image processing device 1 terminates the processing of the flowchart. On the other hand, if the image processing device 1 determines that the endoscopic inspection has not been terminated (Step S108; No), the image processing device 1 returns the process to step S102. Then, the image processing device 1 executes the processing at step S102 to step S107 again.

On the other hand, at step S100, if the captured images Ic at the time of the previous inspection for the same subject are not stored in the captured image storage unit 20 (step S100; No), the acquiring unit 41 acquires the captured image Ic supplied in real time from the endoscope 3 and stores the acquired captured image Ic in the captured image storage unit 20 (step S109). Additionally, the display control unit 46 displays the captured image Ic acquired by the acquiring unit 41 on the display device 2.

Then, the attention part information generating unit 42 determines whether or not an attention part exists based on the image analysis result of the captured image Ic acquired by the acquiring unit 41 from the endoscope 3 or the operation signal 51 supplied from the endoscope 3 (step S110). Then, if the attention part information generating unit 42 determines that an attention part exists (step S110; Yes), the attention part information generating unit 42 generates the attention part information corresponding to the attention part, and stores the generated attention part information in the attention part information storage unit 21 (step S111).

If the process at step S111 is terminated, or there is no attention point (step S110; No), the image processing device 1 determines whether or not the ongoing endoscopic inspection has been terminated (step S112). For example, the image processing device 1 determines that the endoscopic inspection has been terminated when a predetermined input or the like to the input unit 14 or the operation unit 32 is detected. If it is determined that the endoscopic inspection has been terminated (Step S112; Yes), the image processing device 1 terminates the processing of the flowchart. On the other hand, if the endoscopy has not been terminated (Step S112; No), the image processing device 1 continues to perform the processing at step S109 to step S111.

(7) Panoramic Image Generating Process

Next, a panoramic image generating process executed by the panoramic image generating unit 43 at step S101 in FIG. 8 will be specifically described.

Figure 9:
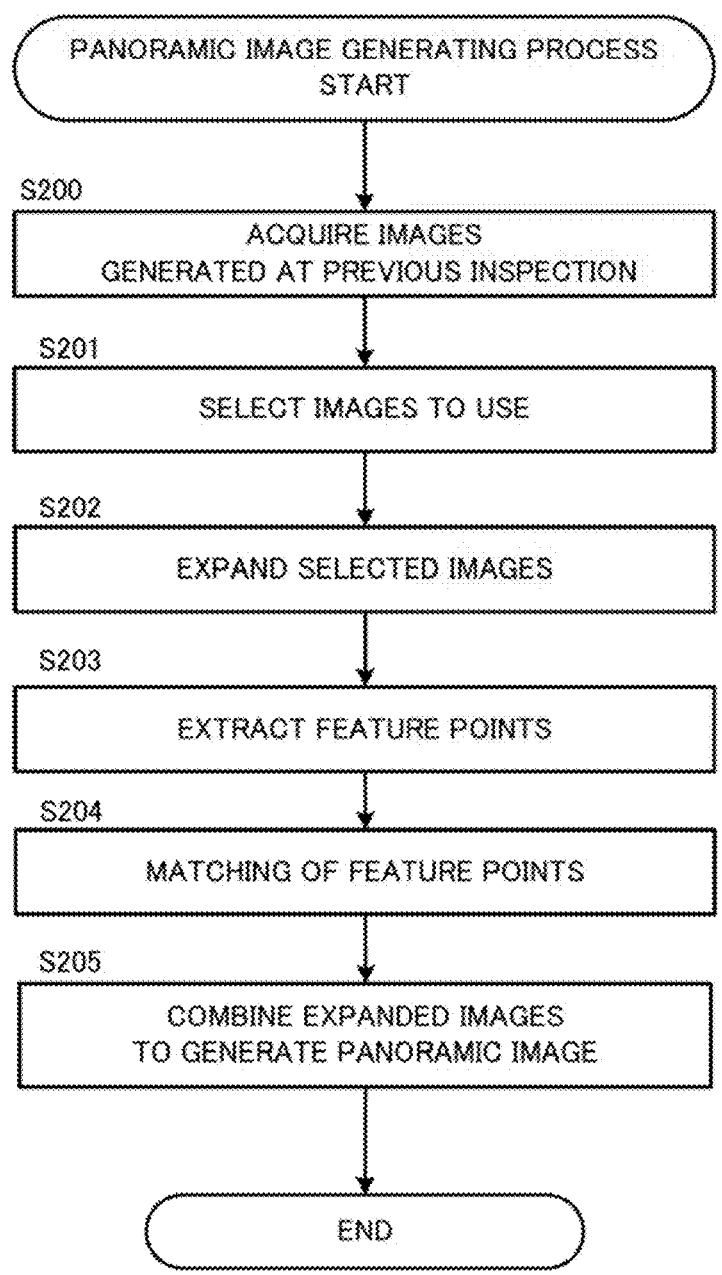
FIG. 9 illustrates an example of a flowchart of a panoramic image generating process.

FIG. 9 is an example of a flowchart of the panoramic image generating process executed by the panoramic image generating unit 43. The panoramic image generating unit 43 executes the processing of the flowchart in FIG. 9 at step S101 of FIG. 8.

For example, the panoramic image generating unit 43 acquires a series of captured images Ic generated during the photographing process (i.e., the insertion process or the ejection process of the endoscope 3) at the previous inspection from the captured image storage unit 20 (step S200). Next, the panoramic image generating unit 43 selects images to be used for generating the panoramic image Ip from the captured images Ic acquired at step S200 (step S201). In this case, for example, the panoramic image generating unit 43 inputs each captured image Ic acquired at step S200 into an inference machine, wherein the inference machine is configured to output inference result regarding blurring or the like is present in an input image which is inputted to the inference machine. Then, the panoramic image generating unit 43 selects images, each of which is inferred by the inference machine that there is no blurring, as the images to be used for generating the panoramic image Ip. In this case, the parameters necessary for the inference machine described above are generated in advance by, for example, training a learning model based on deep learning, and are stored in the memory 12 or the like.

Next, the panoramic image generating unit 43 expands (unfolds) each of the captured images Ic selected at step S201 (step S202). For example, the panoramic image generating unit 43 detects the farthest point corresponding to the position farthest from the viewpoint position in each captured image Ic and performs polar coordinate transformation around the farthest point to thereby generate the expanded captured image Ic (referred to as "expanded image").

Next, the panoramic image generating unit 43 performs the extracting process of the feature points for each expanded image generated at step S202 (step S203). For example, the panoramic image generating unit 43 extracts feature points in each expanded image using any feature extracting algorithm such as AKAZE, SIFT, SURF, and BRISK.

Then, the panoramic image generating unit 43 performs matching of the feature points among the expanded images (step S204). In this case, the panoramic image generating unit 43 detects the feature points having the same feature quantity among the expanded images, and considers the combination of these feature points as the same point, thereby recognizing the correspondence of the feature points among the expanded images. In this case, for example, the panoramic image generating unit 43 matches the feature points among the expanded images using various feature point matching techniques such as RANSAC or K-Nearest Neighbor.

Then, the panoramic image generating unit 43 generates the panoramic image Ip by combining all the expanded images generated at step S202 based on the matching result of the feature points at step S204 (step S205). In this case, the panoramic image generating unit 43 generates the panoramic image Ip in which all the expanded images are combined by non-rigid deformation of the expanded images so that the matched feature points overlap with one another.

It is noted that the panoramic image generating process to be performed by the panoramic image generation unit 43 is not limited to the process shown in FIG. 9, and any process may be used as long as it converts an annular image acquired by capturing a lumen organ or an inside of a cylindrical structure having a structure equivalent thereto into a panoramic image. For example, JP 2013-84156 discloses a process of converting an annular image into a panoramic image.

(8) Distance Calculation Process

Next, a specific description will be given of the distance calculation process executed by the distance calculating unit 45 at step S104 in FIG. 8.

Figure 10:
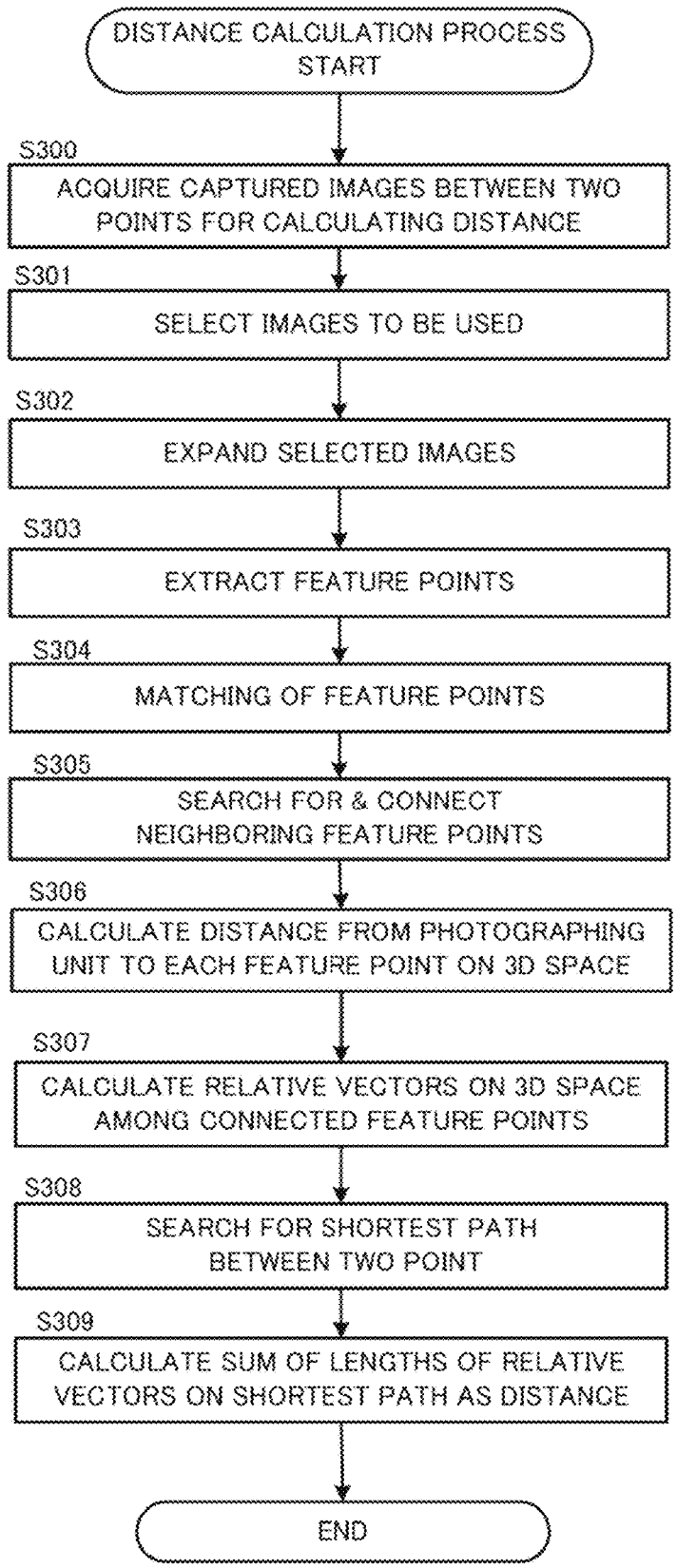
FIG. 10 illustrates an example of a flowchart of a distance calculation process.

FIG. 10 is an example of a flowchart of the distance calculation process executed by the distance calculating unit 45. The panoramic image generating unit 43 executes the processing of the flowchart in FIG. 10 at step S104 of FIG. 8.

First, the distance calculating unit 45 acquires the captured images Ic between the two points subjected to distance calculation from the captured image storage unit 20 which stores the series of captured images Ic generated during the previous endoscopic inspection (step S300). In this case, for example, the distance calculating unit 45 acquires captured images Ic in which the two points subjected to distance calculation are photographed, respectively and other captured images Ic, which are generated between the captured images Ic corresponding to the two points, from the captured image storage unit 20.

For example, a case of calculating the distance from the insertion position of the endoscope 3 to the photographed position will be considered herein. In this case, the distance calculating unit 45 identifies the captured image Ic whose photographing range includes the insertion position of the endoscope 3 and a captured image Ic corresponding to the latest captured image Ic acquired in the ongoing endoscopic inspection, respectively, from a series of captured images Ic generated during the previous endoscopic inspection. Then, the distance calculating unit 45 acquires from the captured image storage unit 20 the identified two captured images Ic and the captured images Ic generated between them as the captured images Ic between the two points subjected to distance calculation.

When calculating the distance from the insertion position of the endoscope 3 to the photographed position, the distance calculating unit 45 may acquire the captured images Ic generated in the ongoing endoscopic inspection instead of acquiring the captured images Ic generated in the previous endoscopic inspection. In this case, the distance calculating unit 45 acquires at step S300 the captured images Ic acquired in the period from the start time of the present endoscopic inspection to the present time. Even in this case, the distance calculating unit 45 can calculate the distance from the insertion position of the endoscope 3 to the photographed position.

Next, the distance calculating unit 45 executes the same processing as step S201 to step S204 in the panoramic image generating process shown in FIG. 9 for the captured images Ic acquired at step S300. Specifically, the distance calculating unit 45 selects images to be used for distance calculation (i.e., images without blurring or the like) from the captured images Ic acquired at step S300 (step S301). Next, the distance calculating unit 45 expands (unfold) each of the captured images Ic selected at step S301 (step S302). Then, the distance calculating unit 45 performs the extracting process of the feature points for the respective expanded images generated at step S302 (step S303). Then, the distance calculating unit 45 matches the feature points having the same feature quantity among the expanded images through the feature point matching method, and recognizes the correspondence among the expanded images (step S304).

For example, the panoramic image generating unit 43 may store the processing results (for example, the expanded image, the information of the feature points, and the matching result of the feature points) at step S201 to step S204 in the panoramic image generating process in association with the respective captured images Ic stored in the captured image storage unit 20. In this case, instead of executing the process at step S301 to step S304, the distance calculating unit 45 can obtain the processing results at step S301 to step S304 by referring to the processing results associated with the captured images Ic by the panoramic image generating unit 43.

Next, the distance calculating unit 45 searches for a neighboring feature point with respect to each feature point extracted at step S303 and connects the neighboring feature point to the each feature point (step S305). In this case, the distance calculating unit 45 searches for a neighboring feature point in the vicinity of each feature point of each expanded image, and provides a link for connecting the feature points adjacent to each other. Details of this process will be described later with reference to FIG. 11.

Next, the distance calculating unit 45 calculates the distance of each feature point from the photographing unit on the three-dimensional space (step S306). In this case, for example, the distance calculating unit 45 calculates the distance of each feature point from the photographing unit on the three-dimensional space based on the depth estimation algorithm using machine learning. Details of this process will be described with reference to FIG. 12.

Then, the distance calculating unit 45 calculates relative vectors on the three-dimensional space among the feature points connected at step S305, based on the expanded images acquired at step S302, the parameters of the photographing unit, and the distance between the feature points calculated at step S306 (step S307). Details of this process will be described with reference to FIGS. 13 and 14.

Next, the distance calculating unit 45 searches for the shortest path between the two points subjected to distance calculation (step S308). In this case, the distance calculating unit 45 connects the links among the feature points which exist between the two points subjected to distance calculation to thereby form paths between the two points subjected to distance calculation. Then, the distance calculating unit 45 determines the shortest path to be such a path that the sum of the lengths of relative vectors corresponding to links constituting the path is minimized. Then, the distance calculating unit 45 calculates, as the distance between the two points subjected to distance calculation, the sum of the lengths of the relative vectors corresponding to the links constituting the shortest path (step S309). Details of the process at step S308 and step S309 will be described with reference to FIGS. 15 and 16.

Figure 11A:
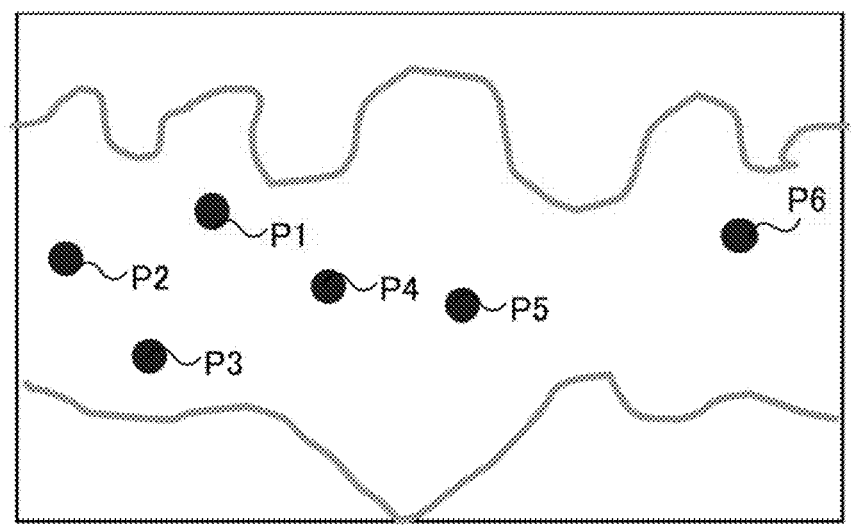
FIG. 11A illustrates extracted feature points on an expanded image.
Figure 11B:
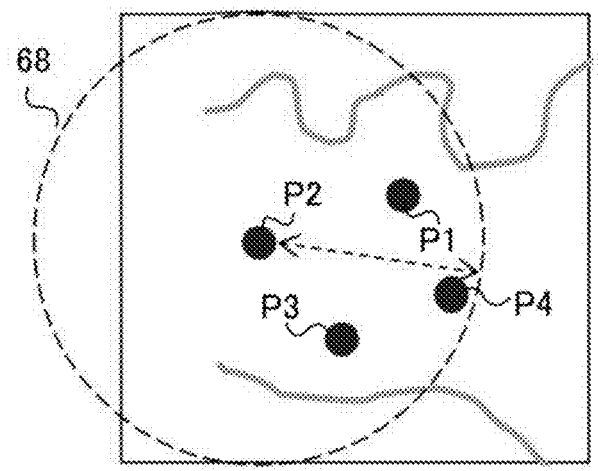
FIG. 11B illustrates an enlarged image at and around a feature point P2.

Here, a description will be given of the searching for and connecting neighboring feature points at step S305 with reference to FIGS. 11A to 11C. FIG. 11A is a diagram illustrating feature points "P1" to "P6" extracted at step S303 on the expanded image generated from a captured image Ic. FIG. 11B is an image acquired by enlarging the vicinity of the feature point P2.

In this case, at step S305, the distance calculating unit 45 searches for the neighboring feature points that are within a predetermined distance (a predetermined pixel) on the expanded image for each of the feature points P1 to P6. For example, when searching for neighboring feature points of the feature points P2, as shown in FIG. 11B, the distance calculating unit 45 searches for the feature points existing in the circle 68 that has a radius of a predetermined distance (see arrow) from the feature points P2. Then, in this case, the distance calculating unit 45 regards the feature points P1, P3, and P4 as the neighboring feature points of the feature points P2, respectively.

Figure 11C:
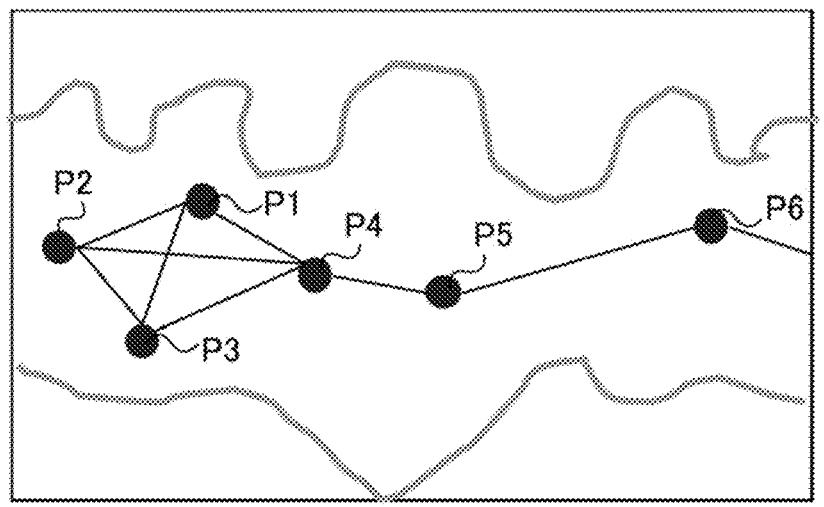
FIG. 11C illustrates an expanded image in which pairs of feature points serving as neighboring feature points are connected by lines.

FIG. 11C shows the expanded image in which each pair of feature points serving as the neighboring feature points is connected by line. As shown in FIG. 11C, the distance calculating unit 45 provides links among the feature points serving as neighboring feature points. For example, since the neighboring feature points of the feature point P2 are the feature points P1, P3, and P4, each link is provided between the feature points P2 and each of the feature points P1, P3, and P4. Then, the distance calculating unit 45 executes the process shown in FIGS. 11A to 11C for all the expanded images generated at step S302.

Figure 12:
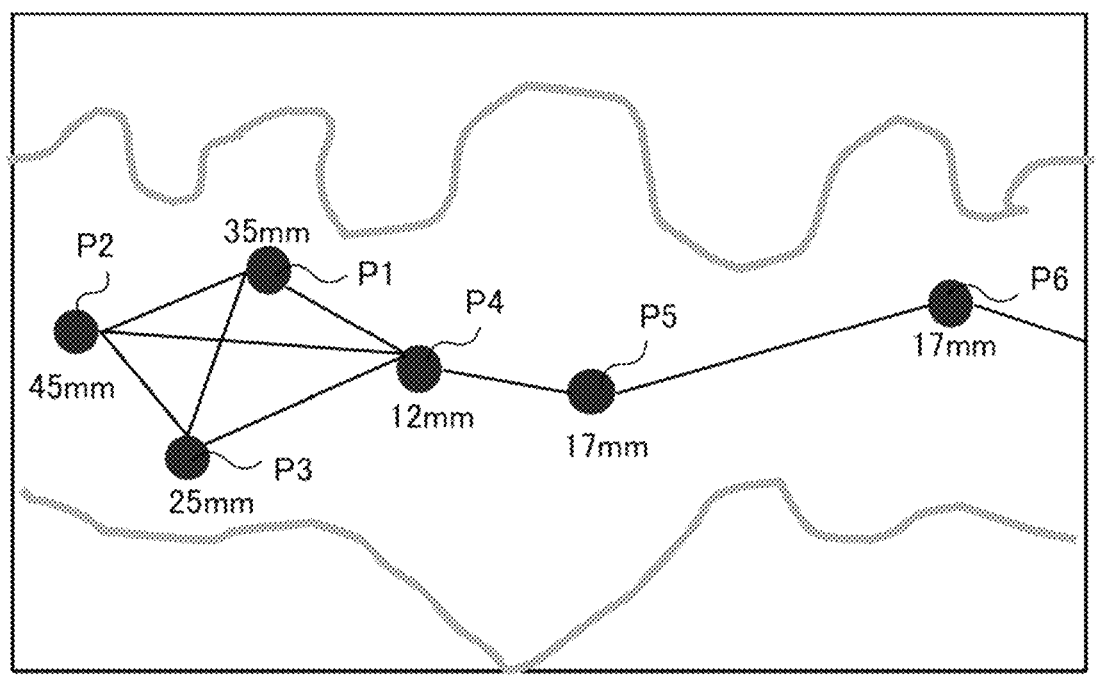
FIG. 12 illustrates an expanded image in which a distance on the three-dimensional space between a photographing unit and each feature point is indicated for each feature point.

Next, a description will be given of the calculation method of the distance on the three-dimensional space from the photographing unit to each feature point at step S306. FIG. 12 shows an expanded image that explicitly indicates the distance from the photographing unit to each of the feature points P1 to P6 on the three-dimensional space.

For example, the distance calculating unit 45 inputs an expanded image to an inference machine, wherein the inference machine is configured to infer the distance from the photographing unit to each pixel (or sub-pixel) of an input image, which is inputted to the inference machine. Then, the distance calculating unit 45 acquires the distance from the photographing unit to each feature point on the three-dimensional space by referring to the inference value outputted by the inference machine for each pixel corresponding to the each feature point. This inference machine is a learning model learned to infer the distance from the photographing unit to each pixel of the input image. For example, the inference machine is a learning model based on deep learning. In the training process of such a learning model, for example, the distance calculated by photographing a large bowel phantom for training use of an endoscopic doctor with a compound eye camera is used as correct answer data, and an endoscopic image of the large bowel phantom is used as an input image, and these combinations are used as training data. Examples of the machine learning approach for estimating the depth (distance) of each pixel of a captured image include DORN (Deep Ordinal Regression Network for Monocular Depth Estimation).

Next, the calculation of the relative vector on the three-dimensional space between the feature points at step S307 will be described with reference to FIGS. 13 and 14.

Figure 13:
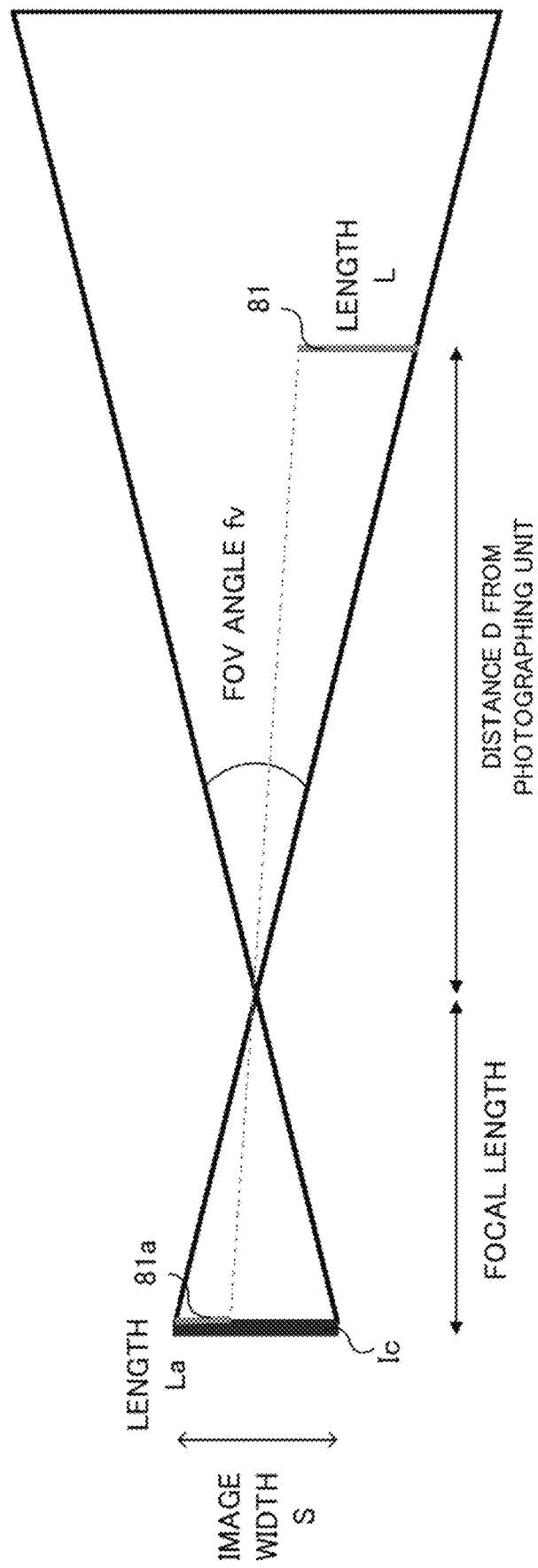
FIG. 13 illustrates the correspondence between the length on a captured image and the actual length in such a case that only one of the horizontal direction or the vertical direction of the captured image is considered.

FIG. 13 is a diagram showing a correspondence relationship between the length (distance) on the captured image Ic and the actual length (distance) when considering only one of the horizontal direction or the vertical direction of the captured image Ic. Here, "L" denotes the length of the rod-shaped object 81 present in the photographing range of the photographing unit, "La" denotes the length (the number of pixels) of the image 81a of the rod-shaped object 81 on the captured image Ic, and "S" denotes the width (the number of pixels) of the captured image Ic. Further, "D" denotes the distance from the photographing unit to the rod-shaped object 81 and "fv" denotes the field-of-view angle (i.e., fov value) which is a parameter of the photographing unit and which is uniquely determined for each lens of the photographing unit. In this case, the length L of the rod-like object 81 is represented by the following equation (1) based on the geometric relationship shown in FIG. 13.

$$L = 2D \cdot \tan(fv/2) \cdot (La/S) \quad (1)$$

In some embodiments, the distance calculating unit 45 may use, instead of the field-of-view angle fv of the photographing unit, another parameter of the photographing unit (e.g., focal length) in order to calculate the length L based on the geometrical relationship shown in FIG. 13 in the same manner.

Figure 14A:
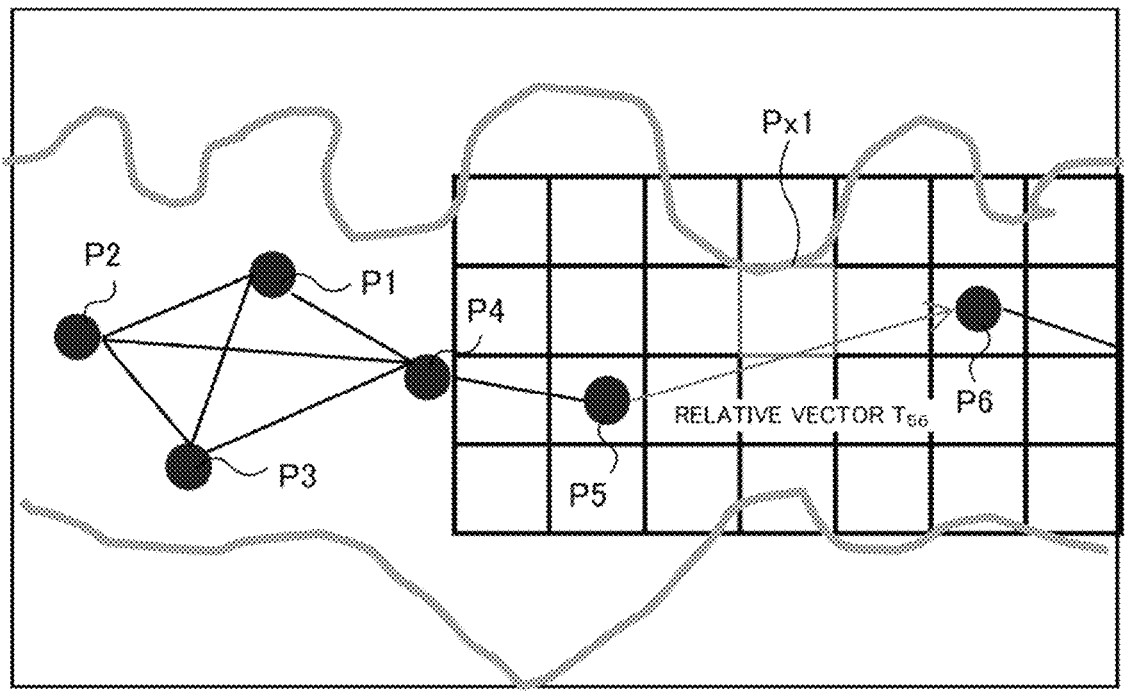
FIG. 14A illustrates the expanded image shown in FIG. 12 in which a part of the area are associated with pixels.

FIG. 14A is an expanded image shown in FIG. 12 in a state where a part of the area is associated with pixels. Here, for convenience of explanation, parallel "x-axis" and "y-axis" are defined to be parallel to the expanded image and perpendicular to each other and "z-axis" is defined to be perpendicular to both the x-axis and the y-axis. Hereafter, as an example, a description will be given of the calculation method of components "Tx", "Ty", and "Tz" each corresponding to x-direction, y-direction, z-direction of the relative vector "$T_{56}$=(Tx, Ty, Tz)" of the link connecting the feature point P5 and the feature point P6.

First, the z-direction component Tz of the relative vector $T_{56}$ is acquired as the difference between the distance "Az" and "Bz" in the depth direction of the feature point P5 and feature point P6, which are the starting and ending points of the relative vector $T_{56}$, as shown in the following equation (2).

$$Tz = Bz - Az \quad (2)$$

Figure 14B:
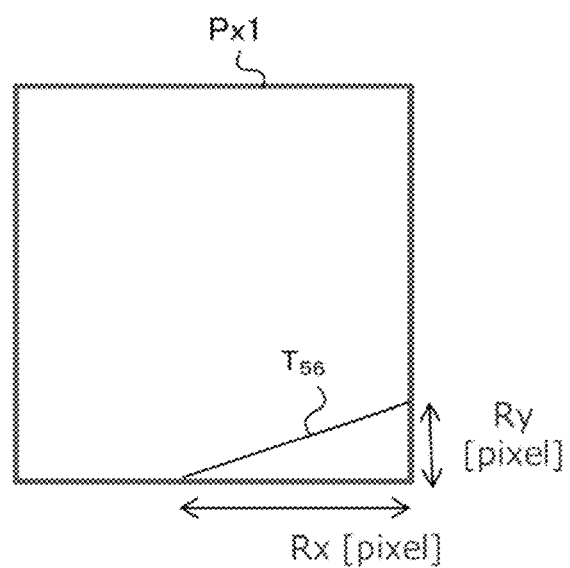
FIG. 14B is an enlarged view of a pixel which explicitly indicates the length of the x-direction and y-direction of a relative vector.

Here, "Dp" denotes the distance between the photographing unit and a point corresponding to the pixel "Pxl" through which the relative vector $T_{56}$ passes, "Rx" and "Ry" (0<Rx, Ry<1) (in units of pixel) denote the length of the relative vector $T_{56}$ in the x-direction and y-direction within the pixel Pxl, respectively. FIG. 14B is an enlarged view of the pixel Pxl explicitly indicating the lengths Rx and Ry of the relative vector $T_{56}$. Further, "fvx" and "fvy" denote the fov values (field-of-view angle) of the photographing unit in the x-direction and y-direction (viewing angle), respectively. "Sx" and "Sy" denote the widths (sizes) of the photographing unit in the x-direction and y-direction of the photographing unit, respectively.

In this case, the x-direction component "Px" and the y-direction component "Py" of the relative vector $T_{56}$ on the target pixel Pxl are represented by the following expressions (3) and (4) in which the above symbols are fitted to the equation (1), respectively.

$$Px = 2Dp \cdot \tan(fvx/2) \cdot (1/Sx) \cdot Rx \quad (3)$$

$$Py = 2Dp \cdot \tan(fvy/2) \cdot (1/Sy) \cdot Ry \quad (4)$$

Then, the distance calculating unit 45 calculates the x-direction component Px and y-direction component Py for each pixel through which the relative vector $T_{56}$ passes and then accumulates them to calculate the x-direction component Tx and y-direction component Ty of the relative vector $T_{56}$, respectively. Namely, the distance calculating unit 45 calculates the x-direction component Tx and y-direction component Ty of the relative vector $T_{56}$ according to the following equations (5) and (6).

$$Tx = \Sigma Px \quad (5)$$

$$Ty = \Sigma Py \quad (6)$$

In this way, on the basis of the expanded image, the parameters of the photographing unit, and the distance between the photographing unit and each feature point, the distance calculating unit 45 can suitably calculate each component Tx, Ty, Tz of the relative vector between the feature points.

Next, the search of the shortest path and the calculation of the distance at step S308 and step S309 will be described with reference to FIGS. 15 and 16.

On the basis of the links connecting the feature points, the distance calculating unit 45 searches for the shortest path between the two points subjected to distance calculation. In this case, the distance calculating unit 45 considers the feature points matched among the expanded images at step S304 as the same point (i.e., points are combined with no distance).

Figure 15:
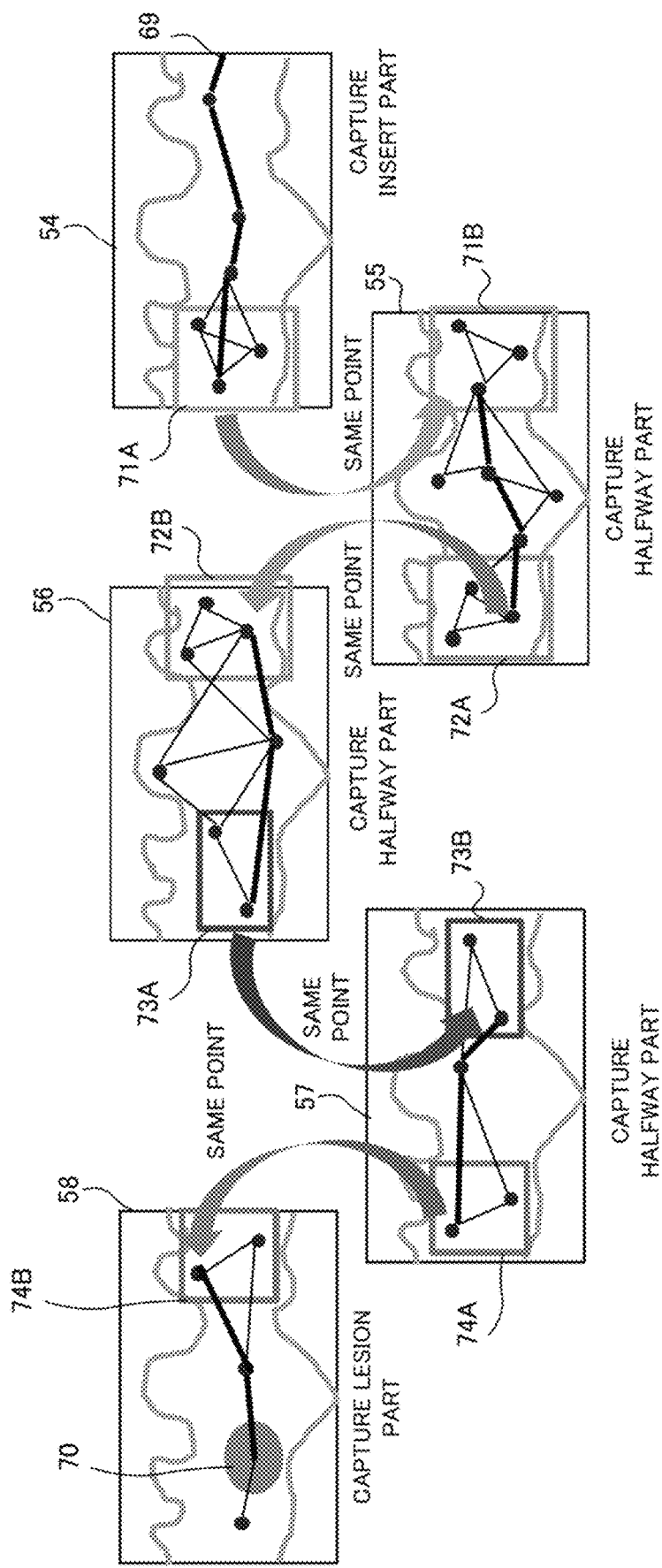
FIG. 15 illustrates the correspondence among feature points in five expanded images to be used when calculating the distance of two points between an insertion part and lesion part.

FIG. 15 illustrate the correspondence among the feature points on the five expanded images 54 to 58 to be used when calculating the distance between the two points from the insertion part 69 to the lesion part 70. FIG. 15 shows, respectively, an expanded image 54 in which an insertion part 69 is photographed, expanded images 55 to 57 in which halfway parts between the insertion part 69 and the lesion part 70 are photographed, and an expanded image 58 in which a lesion part 70 is photographed.

Here, the feature points in the frame 71A on the expanded image 54 are matched with the feature points in the frame 71B on the expanded image 55 in the matching process at step S304. Therefore, in this case, the distance calculating unit 45 regards the feature points in the frame 71A and the feature points in the frame 71B as the same points (i.e., two are coupled at distance 0), respectively. Similarly, the distance calculating unit 45 regards the feature points in the frame 72A on the expanded image 55 and the feature points in the frame 72B on the expanded image 56 as the same points, the feature points in the frame 73A on the expanded image 56 and feature points in the frame 73B on the expanded image 57 as the same points, and the feature points in the frame 74A on the expanded image 57 and the feature points in the frame 74B on the expanded image 58 as the same points.

Figure 16A:
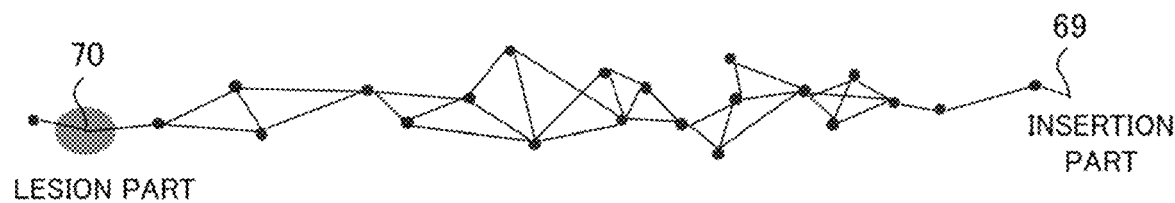
FIG. 16A illustrates a graph showing feature points and links therebetween within the range from the insertion part to the lesion part.

FIG. 16A shows feature points existing between the insertion part 69 and the lesion part 70 and links provided among these feature points. The distance calculating unit 45 determines the matched feature points to be the same point thereby to recognize paths from the insertion part 69 to the lesion part 70 as a graph as shown in FIG. 16A. Then, the distance calculating unit 45 calculates the shortest path from the insertion part 69 to the lesion part 70 by using an arbitrary shortest path search algorithm (for example, the Dijkstra's algorithm) used in the navigation of vehicles or the like. In this case, for example, the distance calculating unit 45 determines the cost of each link to be the norm (length) of the relative vector between the corresponding feature points, and searches for such a path that the total cost of the links constituting the path between the two points subjected to distance calculation is minimized as the shortest path.

Figure 16B:
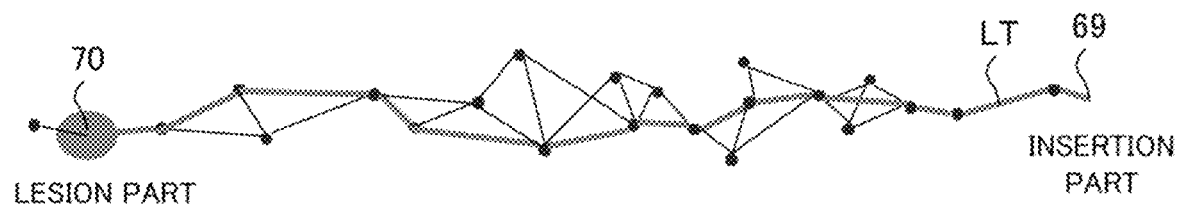
FIG. 16B illustrates the shortest path searched for by a distance calculating unit.
Figure 16C:
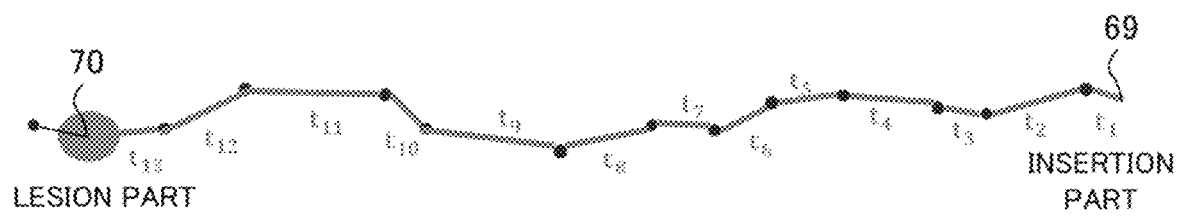
FIG. 16C illustrates the length of each relative vector constituting the shortest path (norm).

FIG. 16B illustrates the shortest path "LT" searched for by the distance calculating unit 45 in FIG. 16A. FIG. 16C illustrates the lengths (norms) "t1" to "t13" of each relative vector constituting the shortest path LT. The distance calculating unit 45 calculates the path length of the shortest path LT by adding the relative vector lengths t1 to t13 corresponding to each link constituting the shortest path LT. Then, the distance calculating unit 45 determines the distance between the insertion part 69 and the lesion part 70 to be the calculated path length (=$"\Sigma_{N=1}^{13} (tN)"$).

In this way, after calculating the relative vectors among the feature points, the distance calculating unit 45 calculates, as the distance between the two points, the path length of such a path that the sum of the length of each relative vector which connects the feature points and which constitutes the path is the smallest among paths formed by connecting these feature points between the two points subjected to distance calculation. Thereby, the distance calculating unit 45 can accurately calculate the length between any two points in the lumen along the lumen.

(9) Modification

Next, a description will be given of modifications of the example embodiment described above. The following modifications may be applied to the example embodiments described above in combination.

(First Modification)

The display control unit 46 may display, on the display device 2 in the ejection process of the endoscope 3, the panoramic image Ip generated based on the captured image Ic acquired in the preceding insertion process of the endoscope 3.

In this case, during the treatment in the lumen in the ejection process, the display control unit 46 generates a panoramic image Ip based on the captured images Ic acquired in the preceding insertion process, and displays the panoramic image Ip on the display device 2. In this example, since the panoramic image Ip is generated without using the captured images Ic generated in the past endoscopic inspection, it does not require the captured images Ic acquired in the past endoscopic inspection for the subject. Therefore, in this modification, even in the first inspection for the subject, when the treatment in the lumen is performed in the ejection process, the display control unit 46 can suitably display the information on the current photographed position and the lesion part and the like in association with the panoramic image Ip.

(Second Modification)

The captured image storage unit 20, the attention part information storage unit 21, and the panoramic image storage unit 22 may be stored in ae storage device separated from the image processing device 1.

Figure 17:
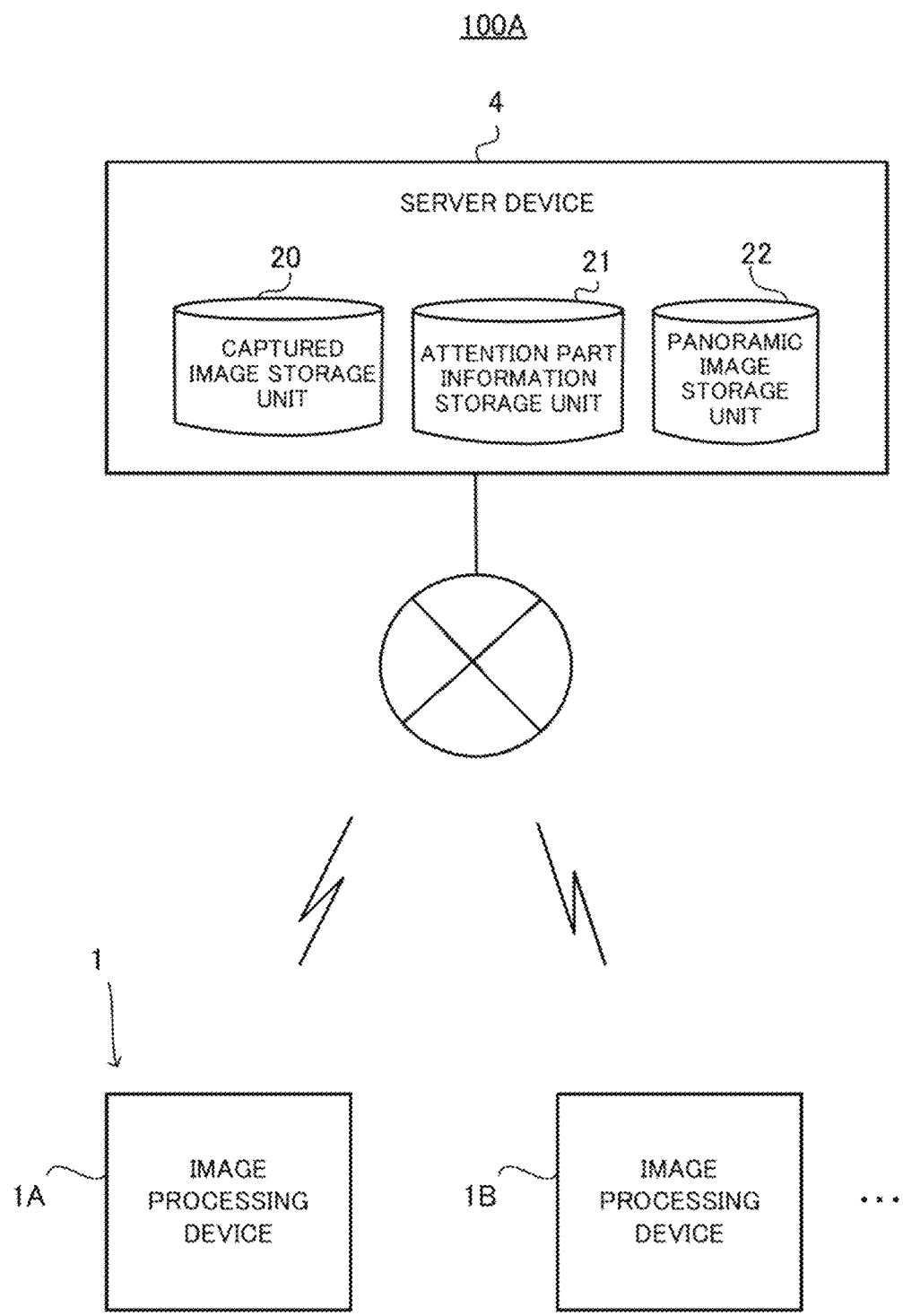
FIG. 17 is a schematic configuration diagram of an endoscopic inspection system according to a modification.

FIG. 17 is a schematic configuration of an endoscopic inspection system 100A according to the second modification. In FIG. 17, for simplicity, the display device 2 and the endoscope 3 and the like are not shown. The endoscopic inspection system 100A illustrated in FIG. 17 includes the captured image storage unit 20, the attention part information storage unit 21, and a server device 4 that stores the panoramic image storage unit 22. The endoscopic inspection system 100A also includes a plurality of image processing devices 1 (1A, 1B, . . . ) capable of data communication with the server device 4 via a network.

In this case, each of the image processing devices 1 refers to and updates the captured image storage unit 20, the attention part information storage unit 21, and the panoramic image storage unit 22 through the network. In this case, the interface 13 of each image processing device 1 includes a communication interface such as a network adapter for performing communication. In this configuration, similarly to the above-described example embodiment, each of the image processing devices 1 can suitably refers to and updates the captured image storage unit 20, the attention part information storage unit 21, and the panoramic image storage unit 22.

Further, in the endoscopic inspection system 100A shown in FIG. 17, the image processing devices 1 share information stored in the captured image storage unit 20, the attention part information storage unit 21, and the panoramic image storage unit 22. Therefore, even when the first endoscopic inspection and the second endoscopic inspection for the same subject are performed using different image processing devices 1, the image processing device 1 used in the second endoscopic inspection can perform each display shown in FIGS. 4 to 7. In this case, the image processing device 1, which has performed the first inspection, generates the panoramic image Ip and stores it in the panoramic image storage unit 22, and the image processing device 1, which performs the second inspection, acquires the panoramic image Ip from the panoramic image storage unit 22 and performs the respective displays shown in FIGS. 4 to 7.

(Third Modification)

The display device 2 may be part of the image processing device 1. In this case, the processor 11 of the image processing device 1 supplies a display signal for displaying the view shown in FIGS. 4 to 7 to a display unit corresponding to the display device 2. The display device 2 may be a projector or the like for projecting an image and therefore it is not limited to a display.

(Fourth Modification)

Information corresponding to the attention part information stored in the attention part information storage unit 21 may be stored in the captured image storage unit 20.

For example, the captured image storage unit 20 may store flag information indicative of an attention part in association with the captured image Ic representing the attention part. In this case, the attention part information storage unit 21 may not exist. Even in this mode, the processor 11 can appropriately recognize the presence of the attention point by referring to the captured image storage unit 20 and reflect it on the display on the display device 2 in the same manner as in the above-described example embodiment.

Further, in FIG. 3, the panoramic image generating unit 43 may supply the generated panoramic image Ip to the display control unit 46 instead of storing the generated panoramic image Ip in the panoramic image storage unit 22. In this mode, the panoramic image storage unit 22 may not exist.

Second Example Embodiment

Figure 18:
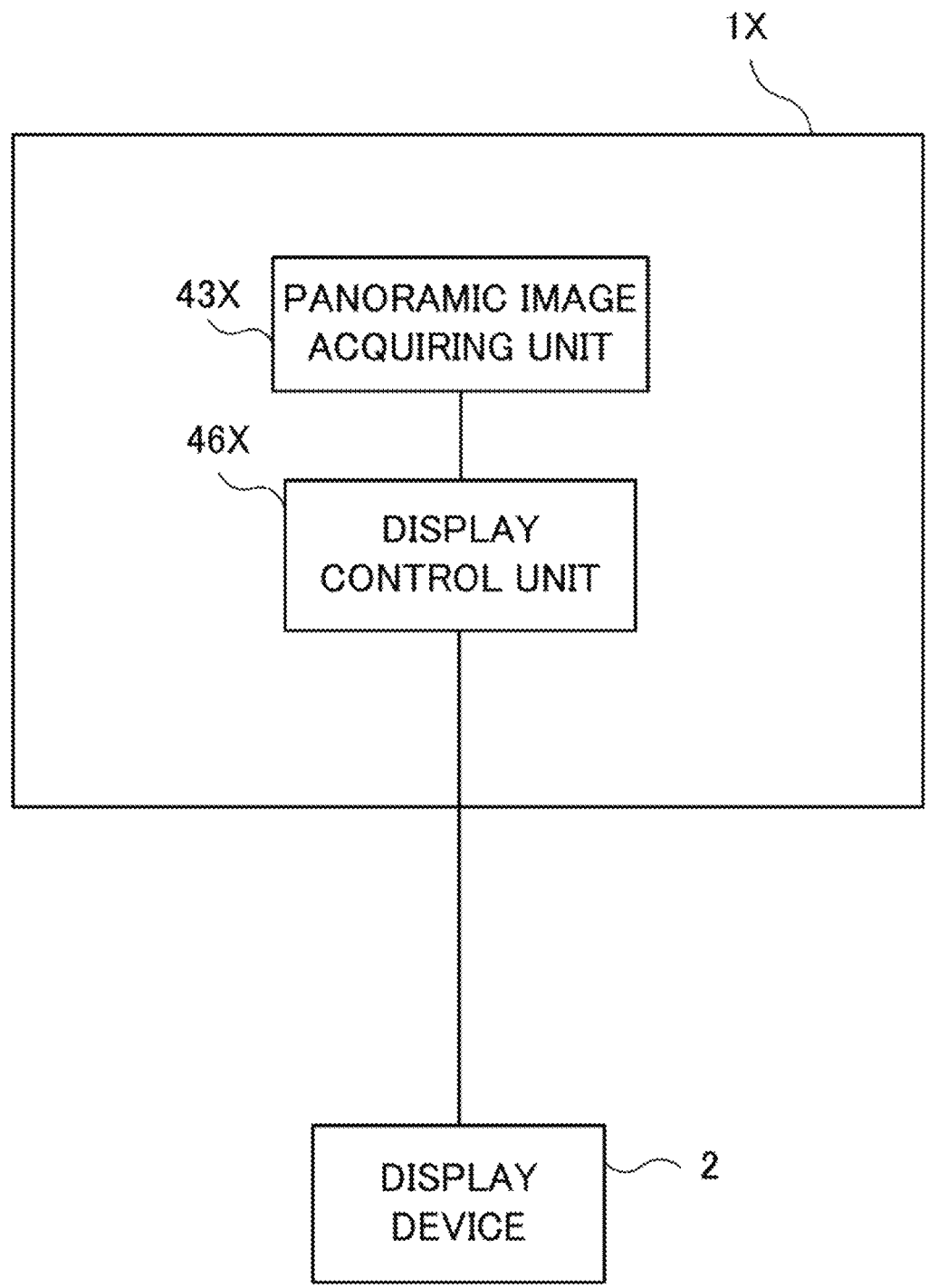
FIG. 18 is a block diagram of an image processing device according to a second example embodiment.

FIG. 18 is a block diagram of the image processing device 1X according to the second example embodiment. The image processing device 1X includes a panoramic image acquiring unit 43X and a display control unit 46X.

The panoramic image acquiring unit 43X acquires a panoramic image Ip, in which a wall surface in a lumen is expanded in a planar shape, based on plural captured images Ic which were acquired by photographing the lumen by a photographing unit provided in an endoscope in a first photographing process. The panoramic image acquiring unit 43X may be, for example, the panoramic image generating unit 43 according to the first example embodiment that generates a panoramic image Ip by performing the panoramic image generating process. In another example, the panorama image acquiring unit 43X may acquire the panorama image Ip generated by another device from the another device or a storage device that stores the panorama image Ip.

The display control unit 46X displays on the display device 2 photographed position information relating to a photographed position of the lumen in a second photographing process in association with the panoramic image Ip. The photographed position information may be, for example, the first photographed position information Itg1 and/or the second photographed position information Itg2 according to the first example embodiment.

According to the second example embodiment, the image processing device 1X can also allow the inspector to suitably grasp the photographed position of the lumen in the second photographing process.

The whole or a part of the example embodiments described above (including modifications, the same applies hereinafter) can be described as, but not limited to, the following Supplementary Notes.

[Supplementary Note 1]
An image processing device comprising:
a panoramic image acquiring unit configured to acquire a panoramic image, in which a wall surface in a lumen is expanded in a planar shape, based on plural captured images which were acquired by photographing the lumen by a photographing unit provided in an endoscope in a first photographing process; and
a display control unit configured to display, on a display device, photographed position information in association with the panoramic image, the photographed position information relating to a photographed position of the lumen in a second photographing process.

[Supplementary Note 2]
The image processing device according to Supplementary Note 1,
wherein the display control unit displays, on the display device, information indicating a distance from an insertion position of the endoscope to the photographed position as the photographed position information.

[Supplementary Note 3]
The image processing device according to Supplementary Note 1 or 2, further comprising
a photographed position identifying unit configured to identify the photographed position based on an image photographed in the second photographing process,
wherein the display control unit displays, as the photographed position information, a mark indicating the photographed position identified by the photographed position identifying unit on the panoramic image.

[Supplementary Note 4]
The image processing device according to any one of Supplementary Notes 1 to 3, further comprising
a distance calculating unit configured to calculate a distance between two points in the lumen, based on a parameter of the photographing unit and a distance from the photographing unit to each of plural feature points on the wall surface.

[Supplementary Note 5]
The image processing device according to Supplementary Note 4,
wherein the distance calculating unit acquires the distance from the photographing unit to a feature point by inputting an image in which the feature point is photographed to an inference machine, the inference machine being learned to output, for an input image, a distance from the photographing unit to a photographed object of the input image.

[Supplementary Note 6]
The image processing device according to Supplementary Note 4 or 5,
wherein the distance calculating unit
calculates relative vectors among the plural feature points based on the parameter of the photographing unit, the distance from the photographing unit to the each of the plural feature points, and an image in which the each of the plural feature point is photographed, and
calculates, as the distance between the two points, the smallest sum of lengths of the relative vectors connecting feature points constituting a path among paths between the two points specified by connecting the plural feature points.

[Supplementary Note 7]
The image processing device according to Supplementary Note 6,
wherein the distance calculating unit detects a combination of feature points indicative of a same position among images in which the plural feature points are photographed, and considers the combination of the feature points as a same feature point.

[Supplementary Note 8]
The image processing device according to any one of Supplementary Notes 1 to 7,
wherein the display control unit displays a mark indicating an attention point on the panoramic image on the display device.

[Supplementary Note 9]
The image processing device according to Supplementary Note 8,
wherein the display control unit displays, on the display device, information indicating at least one of
a distance from the photographed position to the attention point, or
a distance from an insertion position of the endoscope to the attention point.

[Supplementary Note 10]

The image processing device according to Supplementary Note 8 or 9,
wherein the attention point is a lesion part or a contact point with which the endoscope got contact in an insertion process of the endoscope.

[Supplementary Note 11]

The image processing device according to any one of Supplementary Notes 8 to 10,
wherein the display control unit outputs an attention when a distance from the photographed position to the attention point is equal to or less than a predetermined distance.

[Supplementary Note 12]

The image processing device according to any one of Supplementary Notes 1 to 11,
wherein the panoramic image acquiring unit generates the panoramic image based on plural images photographed in an ejection process of the endoscope.

[Supplementary Note 13]

The image processing device according to any one of Supplementary Notes 1 to 12,
wherein the display control unit displays information indicating a current direction of the photographing unit on the display device.

[Supplementary Note 14]

The image processing device according to any one of Supplementary Notes 1 to 13,
wherein the display control unit outputs instruction information relating to adjustment of a direction of the photographing unit.

[Supplementary Note 15]

The image processing device according to any one of Supplementary Notes 1 to 14,
wherein the display control unit displays, on the display device, the panoramic image based on plural images photographed in the second photographing process together with the panoramic image based on the plural images photographed in the first photographing process.

[Supplementary Note 16]

A control method executed by an image processing device, the control method comprising:
acquiring a panoramic image, in which a wall surface in a lumen is expanded in a planar shape, based on plural captured images which were acquired by photographing the lumen by a photographing unit provided in an endoscope in a first photographing process; and
displaying, on a display device, photographed position information in association with the panoramic image, the photographed position information relating to a photographed position of the lumen in a second photographing process.

[Supplementary Note 17]

A storage medium storing a program executed by a computer, the program causing the computer to function as:
a panoramic image acquiring unit configured to acquire a panoramic image, in which a wall surface in a lumen is expanded in a planar shape, based on plural captured images which were acquired by photographing the lumen by a photographing unit provided in an endoscope in a first photographing process; and
a display control unit configured to display, on a display device, photographed position information in association with the panoramic image, the photographed position information relating to a photographed position of the lumen in a second photographing process.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All patent and Non-Patent Literatures mentioned in this specification are incorporated by reference in its entirety.

DESCRIPTION OF REFERENCE NUMERALS 1, 1X Image processing device
2 Display device
3 Endoscope
11 Processor
12 Memory
13 Interface
14 Input unit
15 Light source unit
16 Audio output section
20 Captured image storage unit
21 Attention point information storage unit
22 Panoramic image storage unit
100, 100A Endoscopic inspection system

What is claimed is:

1. An image processing device comprising:
at least one memory configured to store instructions; and
at least one processor configured to execute the instructions to:
acquire a panoramic image in which a wall surface in a lumen is expanded in a planar shape, based on plural captured images acquired by photographing the lumen using a photographing unit provided in an endoscope in a first photographing process;
calculate a distance between a photographed position of the lumen in a second photographing process and a point in the lumen, based on a parameter of the photographing unit and a distance from the photographing unit to each of plural feature points on the wall surface;
calculate relative vectors among the plural feature points based on the parameter of the photographing unit, the distance from the photographing unit to the each of the plural feature points, and an image in which the each of the plural feature points is photographed,
wherein the distance between the photographed position and the point in the lumen is calculated as a smallest sum of lengths of the relative vectors connecting the feature points of any of plural paths between the photographed position and the point in the lumen that are each specified by connecting different feature points; and
display, on a display device, photographed position information in association with the panoramic image, the photographed position information including the calculated distance between the photographed position and the point.

2. The image processing device according to claim 1,
wherein the at least one processor is configured to execute the instructions to display, on the display device, information indicating a distance from an insertion position of the endoscope to the photographed position, as the photographed position information.

3. The image processing device according to claim 1,
wherein the at least one processor is configured to execute the instructions to further identify the photographed position based on an image photographed in the second photographing process,
wherein the at least one processor is configured to execute the instructions to display, as the photographed position information, a mark indicating the identified photographed position on the panoramic image.

4. The image processing device according to claim 1,
wherein the at least one processor is configured to execute the instructions to acquire the distance from the photographing unit to each of the plural feature points by inputting the image in which the each of the plural feature points is photographed to an inference machine, the inference machine trained using machine learning to output, for an input image, a distance from the photographing unit to a photographed object of the input image.

5. The image processing device according to claim 1,
wherein the at least one processor is configured to execute the instructions to detect a combination of feature points indicative of a same position among images in which the plural feature points are photographed, and consider the combination of the feature points as a same feature point.

6. The image processing device according to claim 1,
wherein the at least one processor is configured to execute the instructions to display a mark indicating an attention point on the panoramic image on the display device.

7. The image processing device according to claim 6,
wherein the at least one processor is configured to execute the instructions to display, on the display device, information indicating at least one of
a distance from the photographed position to the attention point, or
a distance from an insertion position of the endoscope to the attention point.

8. The image processing device according to claim 6,
wherein the attention point is a lesion part or a contact point with which the endoscope got contact in an insertion process of the endoscope.

9. The image processing device according to claim 6,
wherein the at least one processor is configured to execute the instructions to output an attention when a distance from the photographed position to the attention point is equal to or less than a predetermined distance.

10. The image processing device according to claim 1,
wherein the at least one processor is configured to execute the instructions to generate the panoramic image based on plural images photographed in an ejection process of the endoscope.

11. The image processing device according to claim 1,
wherein the at least one processor is configured to execute the instructions to display information indicating a current direction of the photographing unit on the display device.

12. The image processing device according to claim 1,
wherein the at least one processor is configured to execute the instructions to output instruction information relating to adjustment of a direction of the photographing unit to support decision-making by an inspector.

13. The image processing device according to claim 1,
wherein the at least one processor is configured to execute the instructions to display, on the display device, the panoramic image based on plural images photographed in the second photographing process together with the panoramic image based on the plural images photographed in the first photographing process.

14. The image processing device according to claim 1,
wherein the at least one processor is configured to execute the instructions to calculate a distance between the photographed position and a lesion part in the lumen, and display the photographed position information including the distance between the photographed position and the lesion part.

15. The image processing device according to claim 1,
wherein the at least one processor is configured to execute the instructions to calculate the relative vectors among the plural feature points based on a field-of-view angle of the photographing unit, the distance from the photographing unit to the each of the plural feature points, and an expanded captured image in which the each of the plural feature points is photographed.

16. A control method executed by an image processing device, the control method comprising:
acquiring a panoramic image in which a wall surface in a lumen is expanded in a planar shape, based on plural captured images acquired by photographing the lumen using a photographing unit provided in an endoscope in a first photographing process;
calculating a distance between a photographed position of the lumen in a second photographing process and a point in the lumen, based on a parameter of the photographing unit and a distance from the photographing unit to each of plural feature points on the wall surface;
calculating relative vectors among the plural feature points based on the parameter of the photographing unit, the distance from the photographing unit to the each of the plural feature points, and an image in which the each of the plural feature points is photographed,
wherein the distance between the photographed position and the point in the lumen is calculated as a smallest sum of lengths of the relative vectors connecting the feature points of any of plural paths between the photographed position and the point in the lumen that are each specified by connecting different feature points; and
displaying, on a display device, photographed position information in association with the panoramic image, the photographed position information including the calculated distance between the photographed position and the point.

17. A non-transitory computer readable storage medium storing a program executable by a computer to:
acquire a panoramic image in which a wall surface in a lumen is expanded in a planar shape, based on plural captured images acquired by photographing the lumen using a photographing unit provided in an endoscope in a first photographing process;
calculate a distance between a photographed position of the lumen in a second photographing process and a point in the lumen, based on a parameter of the photographing unit and a distance from the photographing unit to each of plural feature points on the wall surface;
calculate relative vectors among the plural feature points based on the parameter of the photographing unit, the distance from the photographing unit to the each of the plural feature points, and an image in which the each of the plural feature points is photographed,
wherein the distance between the photographed position and the point in the lumen is calculated as a smallest sum of lengths of the relative vectors connecting the feature points of any of plural paths between the photographed position and the point in the lumen that are each specified by connecting different feature points; and display, on a display device, photographed position information in association with the panoramic image, the photographed position information including the calculated distance between the photographed position and the point.

* * * * *